(12) United States Patent
Hu et al.

(10) Patent No.: US 10,081,672 B2
(45) Date of Patent: Sep. 25, 2018

(54) ANTI-RICIN ANTIBODIES AND USES THEREOF

(71) Applicant: Her Majesty the Queen in Right of Canada, as represented by the Minister of National Defence, Ottawa (CA)

(72) Inventors: Wei-Gang Hu, Medicine Hat (CA); Laurel M. Negrych, Medicine Hat (CA); Damon Chau, Medicine Hat (CA); Junfei Yin, Medicine Hat (CA); Scott J. Jager, Dunmore (CA); John W. Cherwonogrodzky, Medicine Hat (CA)

(73) Assignee: National Research Council of Canada, Ottawa, ON ( * ) Notice: Subject to any disclaimer, the term of this patent is extended or adjusted under 35 U.S.C. 154(b) by 0 days.

(21) Appl. No.: 15/088,944

(22) Filed: Apr. 1, 2016

(65) Prior Publication Data

US 2016/0280773 A1  Sep. 29, 2016

Related U.S. Application Data

(62) Division of application No. 14/122,366, filed as application No. PCT/CA2012/000092 on Jan. 31, 2012, now Pat. No. 9,309,305.

(60) Provisional application No. 61/495,544, filed on Jun. 10, 2011.

(51) Int. Cl.
| | | |
|---|---|---|
| *C07K 16/00* | (2006.01) | |
| *C12P 21/08* | (2006.01) | |
| *C07K 16/16* | (2006.01) | |
| *C07K 16/28* | (2006.01) | |
| *A61K 39/395* | (2006.01) | |
| *A61K 39/00* | (2006.01) | |

(52) U.S. Cl.
CPC ........ *C07K 16/16* (2013.01); *A61K 39/39575* (2013.01); *C07K 16/28* (2013.01); *A61K 2039/505* (2013.01); *A61K 2039/507* (2013.01); *A61K 2039/545* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2006/0051355 A1* 3/2006 van Oosterhout ............... A61K 47/48561
424/183.1

OTHER PUBLICATIONS

Rudikoff et al (Proc Natl Acad Sci USA 1982 vol. 79 p. 1979).*
Van de Loo et al. (Proc. Natl. Acad. Sci 1995).*
Extended European Search Report dated Jun. 9, 2016.
EPO Communication dated Jul. 17, 2017.
OA dated Jul. 19, 2017.

* cited by examiner

*Primary Examiner* — J. Hines
*Assistant Examiner* — Khatol Shahnan Shah
(74) *Attorney, Agent, or Firm* — Roula Thomas

(57) ABSTRACT

The present invention relates to anti-ricin antibodies and uses thereof. More specifically, the invention relates to anti-ricin antibodies and fragments thereof as well as their use in therapy or prophylaxis.

10 Claims, 4 Drawing Sheets

Specification includes a Sequence Listing.

SEQUENCE LISTING

```
<160> NUMBER OF SEQ ID NOS: 42

<210> SEQ ID NO 1
<211> LENGTH: 11
<212> TYPE: PRT
<213> ORGANISM: Mus musculus

<400> SEQUENCE: 1

Lys Ala Ser Gln Asp Ile Lys Gln Tyr Ile Ala
1               5                   10
```

<210> SEQ ID NO 2
<211> LENGTH: 11
<212> TYPE: PRT
<213> ORGANISM: Mus musculus

<400> SEQUENCE: 2

Lys Ala Ser Gln Asp Ile Asn Asn Tyr Leu Arg
1               5                   10

<210> SEQ ID NO 3
<211> LENGTH: 11
<212> TYPE: PRT
<213> ORGANISM: Mus musculus

<400> SEQUENCE: 3

Lys Ala Ser Gln Asp Ile Lys Lys Tyr Ile Gly
1               5                   10

<210> SEQ ID NO 4
<211> LENGTH: 11
<212> TYPE: PRT
<213> ORGANISM: Mus musculus

<400> SEQUENCE: 4

Lys Ala Ser Gln Asp Val Thr Ala Ala Val Ala
1               5                   10

<210> SEQ ID NO 5
<211> LENGTH: 7
<212> TYPE: PRT
<213> ORGANISM: Mus musculus

<400> SEQUENCE: 5

Tyr Thr Ser Thr Leu Gln Pro
1               5

<210> SEQ ID NO 6
<211> LENGTH: 7
<212> TYPE: PRT
<213> ORGANISM: Mus musculus

<400> SEQUENCE: 6

Arg Ala Asn Arg Leu Val Asp
1               5

<210> SEQ ID NO 7
<211> LENGTH: 7
<212> TYPE: PRT
<213> ORGANISM: Mus musculus

<400> SEQUENCE: 7

Tyr Thr Ser Thr Leu Gln Pro
1               5

<210> SEQ ID NO 8
<211> LENGTH: 7
<212> TYPE: PRT
<213> ORGANISM: Mus musculus

<400> SEQUENCE: 8

Ser Ala Ser Tyr Arg Tyr Thr
1               5

```
<210> SEQ ID NO 9
<211> LENGTH: 8
<212> TYPE: PRT
<213> ORGANISM: Mus musculus

<400> SEQUENCE: 9

Leu Gln Tyr Asp His Leu Tyr Thr
1               5

<210> SEQ ID NO 10
<211> LENGTH: 9
<212> TYPE: PRT
<213> ORGANISM: Mus musculus

<400> SEQUENCE: 10

Leu Gln Tyr Asp Glu Phe Pro Tyr Thr
1               5

<210> SEQ ID NO 11
<211> LENGTH: 8
<212> TYPE: PRT
<213> ORGANISM: Mus musculus

<400> SEQUENCE: 11

Leu Gln Tyr Asp Ser Leu Tyr Thr
1               5

<210> SEQ ID NO 12
<211> LENGTH: 9
<212> TYPE: PRT
<213> ORGANISM: Mus musculus

<400> SEQUENCE: 12

Gln Gln Tyr Tyr Asn Thr Pro Leu Thr
1               5

<210> SEQ ID NO 13
<211> LENGTH: 5
<212> TYPE: PRT
<213> ORGANISM: Mus musculus

<400> SEQUENCE: 13

Ser Tyr Trp Ile Gln
1               5

<210> SEQ ID NO 14
<211> LENGTH: 5
<212> TYPE: PRT
<213> ORGANISM: Mus musculus

<400> SEQUENCE: 14

Glu Tyr Ile Ile Asn
1               5

<210> SEQ ID NO 15
<211> LENGTH: 5
<212> TYPE: PRT
<213> ORGANISM: Mus musculus

<400> SEQUENCE: 15

Asn Tyr Trp Ile Glu
1               5
```

```
<210> SEQ ID NO 16
<211> LENGTH: 5
<212> TYPE: PRT
<213> ORGANISM: Mus musculus

<400> SEQUENCE: 16

Glu His Ile Ile Asn
1               5

<210> SEQ ID NO 17
<211> LENGTH: 17
<212> TYPE: PRT
<213> ORGANISM: Mus musculus

<400> SEQUENCE: 17

Glu Ile Leu Pro Gly Thr Gly Asn Thr Asn Tyr Ser Glu Lys Phe Lys
1               5                   10                  15

Gly

<210> SEQ ID NO 18
<211> LENGTH: 17
<212> TYPE: PRT
<213> ORGANISM: Mus musculus

<400> SEQUENCE: 18

Trp Phe Tyr Pro Gly Ser Gly Asp Ile Lys Tyr Asn Glu Lys Phe Lys
1               5                   10                  15

Asp

<210> SEQ ID NO 19
<211> LENGTH: 17
<212> TYPE: PRT
<213> ORGANISM: Mus musculus

<400> SEQUENCE: 19

Glu Ile Leu Pro Gly Ser Gly Ser Ile Asn Tyr Asp Glu Lys Phe Lys
1               5                   10                  15

Gly

<210> SEQ ID NO 20
<211> LENGTH: 17
<212> TYPE: PRT
<213> ORGANISM: Mus musculus

<400> SEQUENCE: 20

Leu Ile Asn Pro Asn Ser Gly Gly Thr Asn Tyr Asn Gln Lys Phe Lys
1               5                   10                  15

Asp

<210> SEQ ID NO 21
<211> LENGTH: 13
<212> TYPE: PRT
<213> ORGANISM: Mus musculus

<400> SEQUENCE: 21

Cys Glu Gly Glu Gly Tyr Phe Gln Ala Trp Phe Ala Tyr
1               5                   10

<210> SEQ ID NO 22
<211> LENGTH: 11
<212> TYPE: PRT
<213> ORGANISM: Mus musculus
```

-continued

<400> SEQUENCE: 22

Asn Gly Arg Trp Asp Asp Asp Tyr Phe Asp Tyr
1               5                   10

<210> SEQ ID NO 23
<211> LENGTH: 13
<212> TYPE: PRT
<213> ORGANISM: Mus musculus

<400> SEQUENCE: 23

Gln Ala Asn Arg Gly Phe Asp Ser Ala Trp Phe Ala Tyr
1               5                   10

<210> SEQ ID NO 24
<211> LENGTH: 7
<212> TYPE: PRT
<213> ORGANISM: Mus musculus

<400> SEQUENCE: 24

Leu Arg Tyr Asp Ala Ala Tyr
1               5

<210> SEQ ID NO 25
<211> LENGTH: 107
<212> TYPE: PRT
<213> ORGANISM: Mus musculus

<400> SEQUENCE: 25

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Lys Gln Tyr
                20                  25                  30

Ile Ala Trp Tyr Gln Tyr Lys Pro Gly Lys Gly Pro Arg Leu Leu Ile
            35                  40                  45

His Tyr Thr Ser Thr Leu Gln Pro Gly Ile Pro Ser Arg Phe Ser Gly
        50                  55                  60

Ser Gly Ser Gly Arg Asp Tyr Ser Phe Ser Ile Ser Asn Leu Asp Pro
65                  70                  75                  80

Glu Asp Ile Ala Thr Tyr Tyr Cys Leu Gln Tyr Asp His Leu Tyr Thr
                85                  90                  95

Phe Gly Gly Gly Thr Lys Leu Glu Ile Lys Arg
            100                 105

<210> SEQ ID NO 26
<211> LENGTH: 122
<212> TYPE: PRT
<213> ORGANISM: Mus musculus

<400> SEQUENCE: 26

Lys Val Gln Leu Gln Glu Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
                20                  25                  30

Trp Ile Gln Trp Ile Lys Gln Arg Pro Gly His Gly Leu Glu Trp Ile
            35                  40                  45

Gly Glu Ile Leu Pro Gly Thr Gly Asn Thr Asn Tyr Ser Glu Lys Phe
        50                  55                  60

Lys Gly Lys Ala Thr Phe Thr Thr Asp Thr Ser Ser Asn Thr Ala Tyr
65                  70                  75                  80

```
Met His Phe Ser Ser Leu Thr Ser Glu Asp Ser Ala Val Tyr Tyr Cys
                85                  90                  95

Ser Arg Cys Glu Gly Glu Gly Tyr Phe Gln Ala Trp Phe Ala Tyr Trp
            100                 105                 110

Gly Gln Gly Thr Thr Val Thr Val Ser Ser
            115                 120

<210> SEQ ID NO 27
<211> LENGTH: 108
<212> TYPE: PRT
<213> ORGANISM: Mus musculus

<400> SEQUENCE: 27

Asp Ile Val Leu Thr Gln Ser Pro Ser Ser Met Tyr Ala Ser Leu Gly
1               5                   10                  15

Glu Arg Val Thr Ile Thr Cys Lys Ala Ser Gln Asp Ile Asn Asn Tyr
            20                  25                  30

Leu Arg Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Ser Leu Thr Ile Ser Ser Leu Glu Tyr
65                  70                  75                  80

Glu Asp Met Gly Phe Tyr Ser Cys Leu Gln Tyr Asp Glu Phe Pro Tyr
                85                  90                  95

Thr Phe Gly Gly Gly Thr Lys Leu Glu Ile Lys Arg
            100                 105

<210> SEQ ID NO 28
<211> LENGTH: 120
<212> TYPE: PRT
<213> ORGANISM: Mus musculus

<400> SEQUENCE: 28

Glu Val Gln Leu Gln Glu Ser Gly Thr Gly Leu Val Lys Pro Gly Ala
1               5                   10                  15

Ser Val Lys Leu Ser Cys Lys Ala Ser Gly Tyr Thr Phe Thr Glu Tyr
            20                  25                  30

Ile Ile Asn Trp Val Lys Gln Arg Ser Gly Gln Gly Leu Glu Trp Ile
        35                  40                  45

Gly Trp Phe Tyr Pro Gly Ser Gly Asp Ile Lys Tyr Asn Glu Lys Phe
50                  55                  60

Lys Asp Lys Ala Thr Leu Thr Ala Asp Lys Ser Ser Ser Thr Val Tyr
65                  70                  75                  80

Met Glu Leu Ser Arg Leu Thr Ser Glu Asp Ser Ala Val Tyr Phe Cys
                85                  90                  95

Ala Arg Asn Gly Arg Trp Asp Asp Tyr Phe Asp Tyr Trp Gly Gln
            100                 105                 110

Gly Thr Thr Val Thr Val Ser Ser
            115                 120

<210> SEQ ID NO 29
<211> LENGTH: 107
<212> TYPE: PRT
<213> ORGANISM: Mus musculus
```

-continued

<400> SEQUENCE: 29

Asp Ile Gln Met Thr Gln Ser Pro Ser Leu Ser Ala Phe Val Gly
1               5                   10                  15

Gly Lys Val Thr Ile Thr Cys Lys Ala Ser Gln Asp Ile Lys Lys
            20                  25                  30

Ile Gly Trp Tyr Gln Gln Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Ser Leu Tyr Thr
                85                  90                  95

Phe Gly Gly Gly Thr Lys Leu Glu Ile Lys Arg
            100                 105

<210> SEQ ID NO 30
<211> LENGTH: 122
<212> TYPE: PRT
<213> ORGANISM: Mus musculus

<400> SEQUENCE: 30

Lys Val Lys Leu Gln Glu Ser Gly Ala Glu Leu Met Lys Pro Gly Ala
1               5                   10                  15

Ser Val Lys Ile Ser Cys Lys Ser Thr Gly Tyr Thr Phe Ser Asn Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Gly Ser Ile Asn Tyr Asp Glu Lys Phe
    50                  55                  60

Lys Gly Lys Ala Thr Phe Thr Ala Asp Thr Ser Ser Asp Thr Val Tyr
65                  70                  75                  80

Met Phe Leu Ser Gly Leu Thr Ser Glu Asp Ser Ala Val Tyr Tyr Cys
                85                  90                  95

Ala Arg Gln Ala Asn Arg Gly Phe Asp Ser Ala Trp Phe Ala Tyr Trp
            100                 105                 110

Gly Gln Gly Thr Thr Val Thr Val Ser Ser
        115                 120

<210> SEQ ID NO 31
<211> LENGTH: 108
<212> TYPE: PRT
<213> ORGANISM: Mus musculus

<400> SEQUENCE: 31

Asp Ile Glu Leu Thr Gln Ser His Lys Phe Met Ser Thr Ser Val Gly
1               5                   10                  15

Asp Arg Val Ser Ile Thr Cys Lys Ala Ser Gln Asp Val Thr Ala Ala
            20                  25                  30

Val Ala Trp Tyr Gln Gln Lys Pro Gly Gln Ser Pro Lys Leu Leu Ile
        35                  40                  45

His Ser Ala Ser Tyr Arg Tyr Thr Gly Val Pro Asp Arg Phe Thr Gly
    50                  55                  60

Ser Gly Ser Gly Ser Asp Phe Thr Phe Thr Ile Ser Ser Val Gln Ala
65                  70                  75                  80

```
Glu Asp Leu Ala Val Tyr Tyr Cys Gln Gln Tyr Tyr Asn Thr Pro Leu
                85                  90                  95
Thr Phe Gly Ala Gly Thr Lys Leu Glu Leu Lys Arg
            100                 105

<210> SEQ ID NO 32
<211> LENGTH: 116
<212> TYPE: PRT
<213> ORGANISM: Mus musculus

<400> SEQUENCE: 32

Gln Val Gln Leu Gln Glu Ser Gly Pro Glu Leu Val Lys Pro Gly Ala
1               5                   10                  15
Ser Met Lys Ile Ser Cys Lys Ala Ser Gly Tyr Ser Phe Thr Glu His
            20                  25                  30
Ile Ile Asn Trp Val Lys Gln Thr His Arg Glu Asn Leu Glu Trp Ile
        35                  40                  45
Gly Leu Ile Asn Pro Asn Ser Gly Gly Thr Asn Tyr Asn Gln Lys Phe
    50                  55                  60
Lys Asp Lys Ala Thr Leu Thr Val Asp Thr Ala Ser Asn Thr Ala Tyr
65                  70                  75                  80
Met Glu Leu Leu Ser Leu Thr Ser Glu Asp Ser Ala Val Tyr Tyr Cys
                85                  90                  95
Ala Arg Leu Arg Tyr Asp Ala Ala Tyr Trp Gly Gln Gly Thr Thr Val
            100                 105                 110
Thr Val Ser Ser
        115

<210> SEQ ID NO 33
<211> LENGTH: 10
<212> TYPE: PRT
<213> ORGANISM: Artificial Sequence
<220> FEATURE:
<223> OTHER INFORMATION: c-Myc detection tag

<400> SEQUENCE: 33

Glu Gln Lys Leu Ile Ser Glu Glu Asp Leu
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Histidine purification tag

<400> SEQUENCE: 34

His His His His His
1               5

<210> SEQ ID NO 35
<211> LENGTH: 11
<212> TYPE: PRT
<213> ORGANISM: Artificial Sequence
<220> FEATURE:
<223> OTHER INFORMATION: Linker

<400> SEQUENCE: 35

Gly Pro Gly Gly Gly Ser Gly Gly Gly Gly Ser
1               5                   10
```

```
<210> SEQ ID NO 36
<211> LENGTH: 24
<212> TYPE: PRT
<213> ORGANISM: Artificial Sequence
<220> FEATURE:
<223> OTHER INFORMATION: Linker

<400> SEQUENCE: 36

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 37
<211> LENGTH: 98
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg

<210> SEQ ID NO 38
<211> LENGTH: 18
<212> TYPE: PRT
<213> ORGANISM: Homo sapiens

<400> SEQUENCE: 38

Tyr Asp Tyr Gly Met Asp Val Trp Gly Gln Gly Thr Thr Val Thr Val
1               5                   10                  15

Ser Ser

<210> SEQ ID NO 39
<211> LENGTH: 95
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
            85                  90                  95

<210> SEQ ID NO 40
<211> LENGTH: 12
<212> TYPE: PRT
<213> ORGANISM: Homo sapiens

<400> SEQUENCE: 40

Leu Thr Phe Gly Gly Gly Thr Lys Val Glu Ile Lys
1               5                   10

<210> SEQ ID NO 41
<211> LENGTH: 116
<212> TYPE: PRT
<213> ORGANISM: Artificial Sequence
<220> FEATURE:
<223> OTHER INFORMATION: VH of hD9

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ile Ile Asn Trp Val Arg Gln Ala Pro Gly Gln Asn Leu Glu Trp Met
        35                  40                  45

Gly Leu Ile Asn Pro Asn Ser Gly Gly Thr Asn Tyr Asn Gln Lys Phe
    50                  55                  60

Lys Asp Arg Val Thr Met Thr Thr Asp Thr Ser Thr Ser Thr Ala Tyr
65                  70                  75                  80

Met Glu Leu Leu Ser Leu Arg Ser Asp Asp Thr Ala Val Tyr Tyr Cys
            85                  90                  95

Ala Arg Leu Arg Tyr Asp Ala Leu Tyr Trp Gly Gln Gly Thr Thr Val
            100                 105                 110

Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: VL of hD9

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Thr Ala Ala
            20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln Tyr Tyr Asn Thr Pro Leu
                85                  90                  95

Thr Phe Gly Gly Gly Thr Lys Val Glu Ile Lys
               100                 105
```

ANTI-RICIN ANTIBODIES AND USES THEREOF

CROSS-REFERENCE TO RELATED APPLICATIONS

This application is a divisional application of U.S. Ser. No. 14/122,366 filed Nov. 26, 2013, which is a national entry of International Patent Application PCT/CA2012/000092 filed Jan. 31, 2012 and claims the benefit of U.S. Provisional Patent Application U.S. Ser. No. 61/495,544 filed Jun. 10, 2011, the entire contents of all of which are herein incorporated by reference.

FIELD OF THE INVENTION

The present invention relates to anti-ricin antibodies and uses thereof. More specifically, the invention relates to anti-ricin antibodies and fragments thereof as well as their use in therapy or prophylaxis.

BACKGROUND OF THE INVENTION

Ricin is a 60-65 kDa glycoprotein derived from beans of the castor plant (Montanaro et al, 1973). It is a relatively simple toxin consisting of a ricin toxin enzymatic-A (RTA) protein and a ricin toxin lectin-B (RTB) protein linked by a disulfide bond. The RTB is responsible for binding to specific sugar residues on the target cell surface and allows internalizaition of ricin by endocytosis, whereas the RTA enzymatically inactivates the ribosome to irreversibly inhibit protein synthesis. A single molecule of RTA within the cell can completely inhibit protein synthesis, resulting in cell death. Ricin is one of the most potent toxins known for humans, with an $LD_{50}$ of 1-20 mg/kg body weight when ingested and 1-20 μg/kg when inhaled or injected (Audi et al, 2005); this is 400 times more toxic than cobra venom, 1000 times more toxic than cyanide, and 4000 times more toxic than arsenic. Ricin is listed on the Centers for Disease Control and Prevention (Atlanta, USA) Category B threat list and is regarded as a high terrorist risk for civilians. Unfortunately, there is currently no therapeutic or vaccine available against ricin.

The development of therapeutics against ricin has proven elusive. Chemical inhibitors targeting ricin have been developed, but these are limited by the high amounts needed for short-term effects and their own toxicity (Burnett et al, 2005; Miller et al, 2002). Development of vaccines against ricin is ongoing, but to date such vaccines have only partially protected mice against ricin (Smallshaw et al, 2007). Of the different approaches for medical countermeasures, the development of anti-ricin antibodies appears the most promising. Much work has been done on developing antibodies, both polyclonal and monoclonal, as therapeutics against the toxin.

These antibodies were directed against the toxic A-chain (blocking its destructive action to the ribosome) or the lectin B-chain (preventing it from binding to and entering the cell). (Neal et al, 2010; Foxwell B M J et al, 1985)

A sheep anti-ricin F(ab)$_2$ was developed in the United Kingdom for research and development as well as for potential emergency use. However, large amounts, about 50-100 μg of polyclonal antibodies (pAbs) (Neal et al, 2010) or 5-100 μg of mAbs (Hewetson et al, 1993; Foxwell et al, 1985), are needed either to protect or treat a mouse from ricin poisoning within a small window of time, providing significant limitations on survival. For example, 5 μg antibody delivered by the intra-peritoneal (i.p.) route had to be given within 24 h to protect mice before 5×$LD_{50}$ ricin challenge (Neal et al, 2010), while 100 μg of mAb per mouse had to be given within 30 min after 10×$LD_{50}$ ricin challenge (Guo et al, 2006).

It was previously reported that mice could be immunized using increasing doses of ricin, their spleens harvested, and hybridoma created by fusing the lymphocytes with myeloma cells (Furukawa-Stoffer et al, 1999). A poisoning method was then used to select clones that survived in culture medium with ricin because these secreted sufficient amounts of anti-ricin neutralizing mAbs. The antibodies from these clones had high neutralizing activity against ricin, as judged by their binding to the toxin in an enzyme linked immunosorbent assay (ELISA) and by ricin neutralization experiments. HRF4 was identified as the best mAb.

While HRF4 showed promising activity in previous studies, there remains a need in the art for highly effective molecules for neutralization of ricin activity. Such molecules would be advantageous in the development of medical countermeasure therapy.

SUMMARY OF THE INVENTION

The present invention relates to anti-ricin antibodies and uses thereof. More specifically, the invention relates to anti-ricin antibodies and fragments thereof as well as their use in therapy or prophylaxis.

The present invention provides an isolated or purified antibody or fragment thereof, comprising
 a variable light chain comprising
  the sequence of complementarity determining region (CDR) L1 selected from sequences KASQDIKQYIA (SEQ ID NO:1), KASQDINNYLR (SEQ ID NO:2), KASQDIKKYIG (SEQ ID NO:3), and KASQDVTAAVA (SEQ ID NO:4);
  the sequence of CDR L2 selected from sequences YTSTLQP (SEQ ID NO:5), RANRLVD (SEQ ID NO:6), YTSTLQP (SEQ ID NO:7), and SASYRYT (SEQ ID NO:8); and
  the sequence of CDR L3 selected from sequences LQYDHLYT (SEQ ID NO:9), LQYDEFPYT (SEQ ID NO:10), LQYDSLYT (SEQ ID NO:11), and QQYYNTPLT (SEQ ID NO:12), and
 a variable heavy chain comprising
  the sequence of complementarity determining region (CDR) H1 selected from sequences SYWIQ (SEQ ID NO:13), EYIIN (SEQ ID NO:14), NYWIE (SEQ ID NO:15), and EHIIN (SEQ ID NO:16);
  the sequence of CDR H2 selected from sequences EILPGTGNTNYSEKFKG (SEQ ID NO:17), WFYPGSGDIKYNEKFKD (SEQ ID NO:18), EILPGSGSINYDEKFKG (SEQ ID NO:19), and LINPNSGGTNYNQKFKD (SEQ ID NO:20); and
  the sequence of CDR H3 selected from sequences CEGEGYFQAWFAY (SEQ ID NO:21), NGRWDDDYFDY (SEQ ID NO:22), QANRGFDSAWFAY (SEQ ID NO:23), and LRYDAAY (SEQ ID NO:24),
 wherein the antibody or fragment thereof specifically recognizes and binds to ricin.

The isolated or purified antibody or fragment thereof as described above may comprise a variable chain comprising a CDR L1 of sequence KASQDIKQYIA (SEQ ID NO:1), a CDR L2 of sequence YTSTLQP (SEQ ID NO:5), and a CDR L3 of sequence LQYDHLYT (SEQ ID NO:9); and a variable heavy chain comprising CDR H1 of sequence SYWIQ (SEQ ID NO:13), a CDR H2 of sequence EILPGTGNTNYSEKFKG (SEQ ID NO:17), and a CDR H3 of sequence CEGEGYFQAWFAY (SEQ ID NO:21).

In another example, the isolated or purified antibody or fragment thereof may comprise a variable chain comprising a CDR L1 of sequence KASQDINNYLR (SEQ ID NO:2), a CDR L2 of sequence RANRLVD (SEQ ID NO:6), and a CDR L3 of sequence LQYDEFPYT (SEQ ID NO:10); and a variable heavy chain comprising CDR H1 of sequence EYIIN (SEQ ID NO:14), a CDR H2 of sequence WFYPGSGDIKYNEKFKD (SEQ ID NO:18), and a CDR H3 of sequence NGRWDDDYFDY (SEQ ID NO:22).

In a further example, the isolated or purified antibody or fragment thereof as described above may comprise a variable chain comprising a CDR L1 of sequence KASQDIKKYIG (SEQ ID NO:3), a CDR L2 of sequence YTSTLQP (SEQ ID NO:7), and a CDR L3 of sequence LQYDSLYT (SEQ ID NO:11); and a variable heavy chain comprising CDR H1 of sequence NYWIE (SEQ ID NO:15), a CDR H2 of sequence EILPGSGSINYDEKFKG (SEQ ID NO:19), and a CDR H3 of sequence QANRGFDSAWFAY (SEQ ID NO:23).

In an alternative example, the isolated or purified antibody or fragment thereof of as described above may comprise a variable chain comprising a CDR L1 of sequence KASQDVTAAVA (SEQ ID NO:4), a CDR L2 of sequence SASYRYT (SEQ ID NO:8), and a CDR L3 of sequence QQYYNTPLT (SEQ ID NO:12); and a variable heavy chain comprising CDR H1 of sequence EHIIN (SEQ ID NO:16), a CDR H2 of sequence LINPNSGGTNYNQKFKD (SEQ ID NO:20), and a CDR H3 of sequence LRYDAAY (SEQ ID NO:24).

In yet a further alternative, the isolated or purified antibody or fragment thereof as described above may comprise a variable light chain sequence selected from:

```
                                        (SEQ ID NO: 25)
DIQMTQSPSSLSASLGGKVTITCKASQDIKQYIAWYQYKPGKGPRLLIHY

TSTLQPGIPSRFSGSGSGRDYSFSISNLDPEDIATYYCLQYDHLYTFGGG

TKLEIKR;

(SEQ ID NO: 27)
DIVLTQSPSSMYASLGERVTITCKASQDINNYLRWFQQKPGKSPKTLIYR

ANRLVDGVPSRFSGSGSGQDYSLTISSLEYEDMGFYSCLQYDEFPYTFGG

GTKLEIKR;

(SEQ ID NO: 29)
DIQMTQSPSSLSAFVGGKVTITCKASQDIKKYIGWYQQKPGKGPRLLIHY

TSTLQPGIPSRFSGSGSGRDYSFSISNLEPEDIATYYCLQYDSLYTFGGG

TKLEIKR;

(SEQ ID NO: 31)
DIELTQSHKFMSTSVGDRVSITCKASQDVTAAVAWYQQKPGQSPKLLIHS

ASYRYTGVPDRFTGSGSGSDFTFTISSVQAEDLAVYYCQQYYNTPLTFGA

GTKLELKR;
``` and
a sequence substantially identical thereto
and a variable heavy chain sequence selected from:

```
                                        (SEQ ID NO: 26)
KVQLQESGAELMKPGASVKISCKATGYTFSSYWIQWIKQRPGHGLEWIGE

ILPGTGNTNYSEKFKGKATFTTDTSSNTAYMHFSSLTSEDSAVYYCSRCE

GEGYFQAWFAYWGQGTTVTVSS;

(SEQ ID NO: 28)
EVQLQESGTGLVKPGASVKLSCKASGYTFTEYIINWVKQRSGQGLEWIGW

FYPGSGDIKYNEKFKDKATLTADKSSSTVYMELSRLTSEDSAVYFCARNG

RWDDDYFDYWGQGTTVTVSS;

(SEQ ID NO: 30)
KVKLQESGAELMKPGASVKISCKSTGYTFSNYWIEWIKQRPGHGLEWIGE

ILPGSGSINYDEKFKGKATFTADTSSDTVYMFLSGLTSEDSAVYYCARQA

NRGFDSAWFAYWGQGTTVTVSS;

(SEQ ID NO: 32)
QVQLQESGPELVKPGASMKISCKASGYSFTEHIINWVKQTHRENLEWIGL

INPNSGGTNYNQKFKDKATLTVDTASNTAYMELLSLTSEDSAVYYCARLR

YDAAYWGQGTTVTVSS;
``` and
a sequence substantially identical thereto.

The isolated or purified antibody or fragment thereof as described by any of the above may comprise:
the variable light chain sequence:

```
                                        (SEQ ID NO: 25)
DIQMTQSPSSLSASLGGKVTITCKASQDIKQYIAWYQYKPGKGPRLLIHY

TSTLQPGIPSRFSGSGSGRDYSFSISNLDPEDIATYYCLQYDHLYTFGGG

TKLEIKR
``` and the variable heavy chain sequence:

```
                                        (SEQ ID NO: 26)
KVQLQESGAELMKPGASVKISCKATGYTFSSYWIQWIKQRPGHGLEWIGE

ILPGTGNTNYSEKFKGKATFTTDTSSNTAYMHFSSLTSEDSAVYYCSRCE

GEGYFQAWFAYWGQGTTVTVSS;
``` or
the variable light chain sequence:

```
                                        (SEQ ID NO: 27)
DIVLTQSPSSMYASLGERVTITCKASQDINNYLRWFQQKPGKSPKTLIYR

ANRLVDGVPSRFSGSGSGQDYSLTISSLEYEDMGFYSCLQYDEFPYTFGG

GTKLEIKR
``` and the variable heavy chain sequence:

```
                                        (SEQ ID NO: 28)
EVQLQESGTGLVKPGASVKLSCKASGYTFTEYIINWVKQRSGQGLEWIGW

FYPGSGDIKYNEKFKDKATLTADKSSSTVYMELSRLTSEDSAVYFCARNG

RWDDDYFDYWGQGTTVTVSS;
``` or
the variable light chain sequence:

```
                                        (SEQ ID NO: 29)
DIQMTQSPSSLSAFVGGKVTITCKASQDIKKYIGWYQQKPGKGPRLLIHY

TSTLQPGIPSRFSGSGSGRDYSFSISNLEPEDIATYYCLQYDSLYTFGGG

TKLEIKR
``` and the variable heavy chain sequence:

(SEQ ID NO: 30)
KVKLQESGAELMKPGASVKISCKSTGYTFSNYWIEWIKQRPGHGLEWIGE

ILPGSGSINYDEKFKGKATFTADTSSDTVYMFLSGLTSEDSAVYYCARQA

NRGFDSAWFAYWGQGTTVTVSS;

or
the variable light chain sequence:

(SEQ ID NO: 31)
DIELTQSHKFMSTSVGDRVSITCKASQDVTAAVAWYQQKPGQSPKLLIHS

ASYRYTGVPDRFTGSGSGSDFTFTISSVQAEDLAVYYCQQYYNTPLTFGA

GTKLELKR and the variable heavy chain sequence:

(SEQ ID NO: 32)
QVQLQESGPELVKPGASMKISCKASGYSFTEHIINWVKQTHRENLEWIGL

INPNSGGTNYNQKFKDKATLTVDTASNTAYMELLSLTSEDSAVYYCARLR

YDAAYWGQGTTVTVSS, or a sequence substantially identical thereto.

The isolated or purified antibody or fragment thereof of the present invention may be specific for the ricin toxin lectin-B protein. The isolated or purified antibody or fragment thereof of may be an IgG.

The present invention also provides a nucleic acid sequence encoding the isolated or purified antibody or fragment thereof as described herein. The invention also encompasses a vector comprising the nucleic acid molecule just described, and hybridoma cell lines expressing the isolated or purified antibody or fragment thereof described above.

The present invention additionally provides a composition comprising one or more than one antibody or fragment thereof of the present invention and a pharmaceutically acceptable diluent, excipient, or carrier. The composition may be a vaccine composition.

The present invention further provides a method of preventing deleterious effects caused by ricin exposure or of treating exposure to ricin, comprising administering one or more than one antibody or fragment thereof or the composition of the present invention to a subject in need thereof. The subject in need thereof may be a mammal, such as a mouse or a human.

In the method as described above, the one or more than one antibody or fragment thereof or composition comprising same may be administered to the subject several hours following exposure to the ricin toxin to treat ricin exposure. Alternatively, or in addition, the one or more than one antibody or fragment thereof or composition thereof may be administered to the subject several weeks prior to exposure to the ricin toxin to protect the subject against ricin exposure.

Additionally, a combination of antibodies or fragments thereof of the present invention may provide a synergistic effect on ricin-neutralizing activity in the methods as just described. One of the antibodies or fragments thereof may be mAb D9 or a fragment thereof; the second antibody or fragment thereof may be mAb B10 or a fragment thereof.

The present invention further encompasses a method of conferring immunity against ricin comprising administering one or more than one antibody or fragment thereof or a composition of the present invention to a subject in need thereof.

Additionally, the present invention provides a method of identifying hybridoma secreting effective anti-ricin antibodies, comprising:
a) providing hybridoma cells prepared from lymphocytes obtained from mice immunized against ricin;
b) exposing the cells to high amounts of ricin; and
c) identifying the cells that survive exposure step b).

In the method as just described, the mice from which the splenocytes are obtained may have been immunized using multiple lethal doses of ricin. In the above method, the high amount of ricin used in step b) may be in the range of 1 to 10 ng/ml or 1 to 5 ng/ml.

Four hybridoma clones were developed that secreted high-titre anti-ricin IgG antibodies. These mAbs have great potential to be developed as antibody-based therapeutic agents or antibody-gene based vaccines against ricin. All four mAbs were found to have high ricin-neutralization potency both in an in vitro neutrallization assay and an in vivo antibody/ricin co-incubation assay, indicating the strong inhibition of ricin-mediated cell death. Monoclonal antibody D9, found to be exceptionally active in the mouse assay, was further tested for post-exposure therapy and pre-exposure prophylaxis against ricin in vivo. It protected mice not only hours, but also several weeks (at least 6 weeks) before toxin challenge ($5 \times LD_{50}$ of ricin), and rescued mice up to 6 hours after poisoning ($5 \times LD_{50}$ of ricin); additionally, low amounts (0.5 µg) were therapeutic against high amounts of toxin (1 µg of ricin). Antibody D9 also showed synergistic effects with other anti-ricin mAb, as determined by the in vitro neutralization assay. A dose of 5 µg antibody in a mouse is equivalent to 1.4 mg in a human. These results indicate that milligram amounts of specific anti-ricin monoclonal antibody in very small volumes (0.1 ml) may be sufficient to protect first responders or treat ricin-exposed casualties.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein.

DETAILED DESCRIPTION OF THE INVENTION

Figure 1:
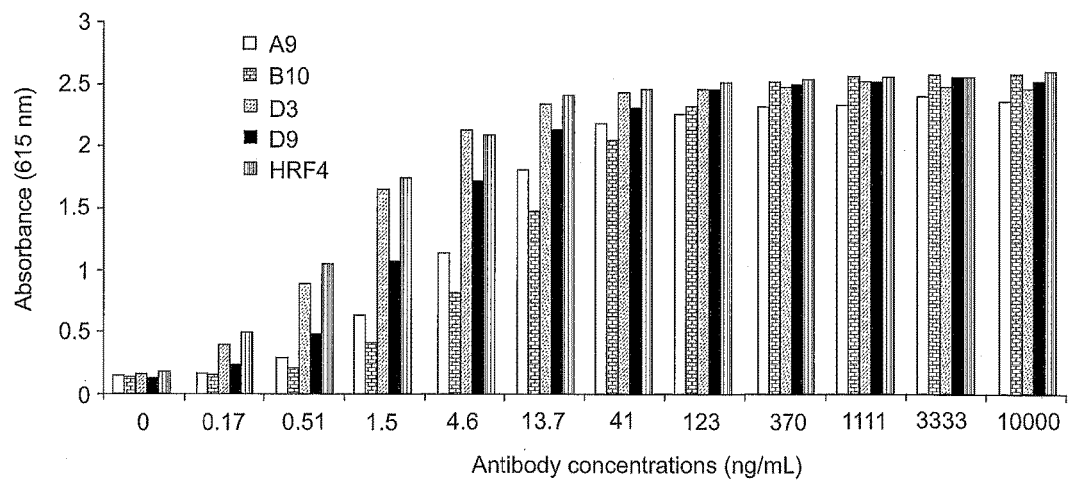
FIG. 1 is a bar graph showing the immunoreactivity of the monoclonal antibodies of the present invention. ELISA experiments were performed on individual antibodies at varying dosages. All the mAb (A9, B10, D3, and D9) bound to ricin in a dose-dependent manner. HRF4 was used as a positive control. The absorbance was read at 615 nm.

The present invention relates to anti-ricin antibodies and uses thereof. More specifically, the invention relates to anti-ricin antibodies and fragments thereof as well as their use in therapy or prophylaxis.

The present invention is directed to anti-ricin antibodies and fragments thereof. The present invention also covers methods of obtaining and identifying antibodies specific for and effective against ricin. The present invention further includes methods of using the anti-ricin antibodies of the invention in anti-ricin therapy and prophylaxis.

The present invention provides an isolated or purified antibody or fragment thereof specific to ricin, comprising a variable light chain comprising
  the sequence of complementarity determining region (CDR) L1 selected from sequences KASQDIKQYIA (SEQ ID N0:1), KASQDINNYLR (SEQ ID N0:2), KASQDIKKYIG (SEQ ID N0:3), and KASQDVTAAVA (SEQ ID N0:4);
  the sequence of CDR L2 selected from sequences YTSTLQP (SEQ ID N0:5), RANRLVD (SEQ ID N0:6), YTSTLQP (SEQ ID N0:7), and SASYRYT (SEQ ID N0:8); and
  the sequence of CDR L3 selected from sequences LQYDHLYT (SEQ ID N0:9), LQYDEFPYT (SEQ ID N0:10), LQYDSLYT (SEQ ID N0:11), and QQYYNTPLT (SEQ ID N0:12), and
a variable heavy chain comprising
  the sequence of complementarity determining region (CDR) H1 selected from sequences SYWIQ (SEQ ID NO:13), EYIIN (SEQ ID NO:14), NYWIE (SEQ ID NO:15), and EHIIN (SEQ ID NO:16);
  the sequence of CDR H2 selected from sequences EILPGTGNTNYSEKFKG (SEQ ID NO:17), WFYPGSGDIKYNEKFKD (SEQ ID NO:18), EILPGSGSINYDEKFKG (SEQ ID NO:19), and LINPNSGGTNYNQKFKD (SEQ ID NO:20); and
  the sequence of CDR H3 selected from sequences CEGEGYFQAWFAY (SEQ ID NO:21), NGRWDDDYFDY (SEQ ID NO:22), QANRGFDSAWFAY (SEQ ID NO:23), and LRYDAAY (SEQ ID NO:24).

The term "antibody", also referred to in the art as "immunoglobulin" (Ig), used herein refers to a protein constructed from paired heavy and light polypeptide chains; various Ig isotypes exist, including IgA, IgD, IgE, IgG, and IgM. When an antibody is correctly folded, each chain folds into a number of distinct globular domains joined by more linear polypeptide sequences. For example, the immunoglobulin light chain folds into a variable ($V_L$) and a constant ($C_L$) domain, while the heavy chain folds into a variable ($V_H$) and three constant ($C_H$, $C_{H2}$, $C_{H3}$) domains. Interaction of the heavy and light chain variable domains ($V_H$ and $V_L$) results in the formation of an antigen binding region (Fv). Each domain has a well-established structure well-known to those of skill in the art.

The light and heavy chain variable regions are responsible for binding the target antigen and can therefore show significant sequence diversity between antibodies. The constant regions show less sequence diversity, and are responsible for binding a number of natural proteins to elicit important biochemical events. The variable region of an antibody contains the antigen binding determinants of the molecule, and thus determines the specificity of an antibody for its target antigen. The majority of sequence variability occurs in six hypervariable regions, three each per variable heavy and light chain; the hypervariable regions combine to form the antigen-binding site, and contribute to binding and recognition of an antigenic determinant. The specificity and affinity of an antibody for its antigen is determined by the structure of the hypervariable regions, as well as their size, shape, and chemistry of the surface they present to the antigen. Various schemes exist for identification of the regions of hypervariability, the two most common being those of Kabat and of Chothia and Lesk. Kabat et al (1991) define the "complementarity-determining regions" (CDR) based on sequence variability at the antigen-binding regions of the VH and VL domains. Chothia and Lesk (1987) define the "hypervariable loops" (H or L) based on the location of the structural loop regions in the VH and VL domains; the numbering for the hypervariable loops is defined as H1: 26-32 or 34; H2: 52-56; and H3: 95-102 (equivalent to CDR3 of Kabat numbering) for VH/VHH domains (Chothia and Lesk, 1987). As these individual schemes define CDR and hypervariable loop regions that are adjacent or overlapping, those of skill in the antibody art often utilize the terms "CDR" and "hypervariable loop" interchangeably, and they may be so used herein. The CDR amino acids in VH and VL regions are defined herein according to the Kabat numbering system (Kabat et al. 1991).

The region outside of the CDR is referred to as the framework region (FR). The FR provides structural integrity to the variable domain and ensures retention of the immunoglobulin fold. This characteristic structure of antibodies provides a stable scaffold upon which substantial antigen-binding diversity can be explored by the immune system to obtain specificity for a broad array of antigens (Padlan et al, 1994). The FR of the variable domain generally show less sequence variability than the hypervariable regions.

An "antibody fragment" as referred to herein may include any suitable antigen-binding antibody fragment known in the art. For example, an antibody fragment may include, but is by no means limited to Fv (a molecule comprising the $V_L$ and $V_H$), single-chain Fv (scFV; a molecule comprising the $V_L$ and $V_H$ connected with by peptide linker), Fab, Fab', F(ab')₂, single domain antibody (sdAb; molecules comprising a single variable domain and 3 CDR), and multivalent presentations of these. The antibody fragment of the present invention may be obtained by manipulation of a naturally-occurring antibody (such as, but not limited to enzymatic digestion), or may be obtained using recombinant methods.

By "specific to ricin", it is meant that the antibody or fragment thereof of the present invention specifically recognizes and binds to ricin. Ricin is a 60-65 kDa glycoprotein derived from beans of the castor plant (Montanaro et al, 1973). It is a relatively simple toxin comprising a ricin toxin enzymatic-A (RTA) protein and a ricin toxin lectin-B (RTB) protein linked by a disulfide bond. The RTB is responsible for binding to specific sugar residues on the target cell surface and allows internalization of ricin by endocytosis, whereas the RTA enzymatically inactivates the ribosome to irreversibly inhibit protein synthesis. The ricin toxin is one of the most potent toxins known for humans.

In a non-limiting example, the isolated or purified antibody or fragment thereof of the present invention may comprise a variable chain comprising a CDR L1 of sequence KASQDIKQYIA (SEQ ID NO:1), a CDR L2 of sequence YTSTLQP (SEQ ID NO:5), and a CDR L3 of sequence LQYDHLYT (SEQ ID NO:9); and a variable heavy chain comprising CDR H1 of sequence SYWIQ (SEQ ID NO:13), a CDR H2 of sequence EILPGTGNTNYSEKFKG (SEQ ID NO:17), and a CDR H3 of sequence CEGEGYFQAWFAY (SEQ ID NO:21). Alternatively, the isolated or purified antibody or fragment thereof of the present invention may comprise variable chain comprising a CDR L1 of sequence KASQDINNYLR (SEQ ID NO:2), a CDR L2 of sequence RANRLVD (SEQ ID NO:6), and a CDR L3 of sequence LQYDEFPYT (SEQ ID NO:10); and a variable heavy chain comprising CDR H1 of sequence EYIIN (SEQ ID NO:14), a CDR H2 of sequence WFYPGSGDIKYNEKFKD (SEQ ID NO:18), and a CDR H3 of sequence NGRWDDDYFDY (SEQ ID NO:22). In yet another alternative, the isolated or purified antibody or fragment thereof of the present invention may comprise variable chain comprising a CDR L1 of sequence KASQDIKKYIG (SEQ ID NO:3), a CDR L2 of sequence YTSTLQP (SEQ ID NO:7), and a CDR L3 of sequence LQYDSLYT (SEQ ID NO:11); and a variable heavy chain comprising CDR H1 of sequence NYWIE (SEQ ID NO:15), a CDR H2 of sequence EILPGSGSINYDEKFKG (SEQ ID NO:19), and a CDR H3 of sequence QANRGFDSAWFAY (SEQ ID NO:23). In a further alternative, the the isolated or purified antibody or fragment thereof of the present invention may comprise variable chain comprising a CDR L1 of sequence KASQDVTAAVA (SEQ ID NO:4), a CDR L2 of sequence SASYRYT (SEQ ID NO:8), and a CDR L3 of sequence QQYYNTPLT (SEQ ID NO:12); and a variable heavy chain comprising CDR H1 of sequence EHIIN (SEQ ID NO:16), a CDR H2 of sequence LINPNSGGTNYNQKFKD (SEQ ID NO:20), and a CDR H3 of sequence LRYDAAY (SEQ ID NO:24).

In one specific, non-limiting example, the isolated or purified antibody or fragment thereof may comprise the variable light chain sequence selected from:

```
                                           (SEQ ID NO: 25)
DIQMTQSPSSLSASLGGKVTITCKASQDIKQYIAWYQYKPGKGPRLLIHY

TSTLQPGIPSRFSGSGSGRDYSFSISNLDPEDIATYYCLQYDHLYTFGGG

TKLEIKR;
```

-continued

```
                                           (SEQ ID NO: 27)
DIVLTQSPSSMYASLGERVTITCKASQDINNYLRWFQQKPGKSPKTLIYR

ANRLVDGVPSRFSGSGSGQDYSLTISSLEYEDMGFYSCLQYDEFPYTFGG

GTKLEIKR;

(SEQ ID NO: 29)
DIQMTQSPSSLSAFVGGKVTITCKASQDIKKYIGWYQQKPGKGPRLLIHY

TSTLQPGIPSRFSGSGSGRDYSFSISNLEPEDIATYYCLQYDSLYTFGGG

TKLEIKR;

(SEQ ID NO: 31)
DIELTQSHKFMSTSVGDRVSITCKASQDVTAAVAWYQQKPGQSPKLLIHS

ASYRYTGVPDRFTGSGSGSDFTFTISSVQAEDLAVYYCQQYYNTPLTFGA

GTKLELKR;
``` and a sequence substantially identical thereto and the variable heavy chain sequence selected from:

```
                                           (SEQ ID NO: 26)
KVQLQESGAELMKPGASVKISCKATGYTFSSYWIQWIKQRPGHGLEWIGE

ILPGTGNTNYSEKFKGKATFTTDTSSNTAYMHFSSLTSEDSAVYYCSRCE

GEGYFQAWFAYWGQGTTVTVSS;

(SEQ ID NO: 28)
EVQLQESGTGLVKPGASVKLSCKASGYTFTEYIINWVKQRSGQGLEWIGW

FYPGSGDIKYNEKFKDKATLTADKSSSTVYMELSRLTSEDSAVYFCARNG

RWDDDYFDYWGQGTTVTVSS;

(SEQ ID NO: 30)
KVKLQESGAELMKPGASVKISCKSTGYTFSNYWIEWIKQRPGHGLEWIGE

ILPGSGSINYDEKFKGKATFTADTSSDTVYMFLSGLTSEDSAVYYCARQA

NRGFDSAWFAYWGQGTTVTVSS;

(SEQ ID NO: 32)
QVQLQESGPELVKPGASMKISCKASGYSFTEHIINWVKQTHRENLEWIGL

INPNSGGTNYNQKFKDKATLTVDTASNTAYMELLSLTSEDSAVYYCARLR

YDAAYWGQGTTVTVSS;
``` and a sequence substantially identical thereto.

In another specific, non-limiting example, the isolated or purified antibody or fragment thereof may comprise the variable light chain sequence

```
                                           (SEQ ID NO: 25)
DIQMTQSPSSLSASLGGKVTITCKASQDIKQYIAWYQYKPGKGPRLLIHY

TSTLQPGIPSRFSGSGSGRDYSFSISNLDPEDIATYYCLQYDHLYTFGGG

TKLEIKR
``` and the variable heavy chain sequence

```
                                           (SEQ ID NO: 26)
KVQLQESGAELMKPGASVKISCKATGYTFSSYWIQWIKQRPGHGLEWIGE

ILPGTGNTNYSEKFKGKATFTTDTSSNTAYMHFSSLTSEDSAVYYCSRCE

GEGYFQAWFAYWGQGTTVTVSS;
``` or
the variable light chain sequence (SEQ ID NO: 27)
DIVLTQSPSSMYASLGERVTITCKASQDINNYLRWFQQKPGKSPKTLIYR

ANRLVDGVPSRFSGSGSGQDYSLTISSLEYEDMGFYSCLQYDEFPYTFGG

GTKLEIKR and the variable heavy chain sequence (SEQ ID NO: 28)
EVQLQESGTGLVKPGASVKLSCKASGYTFTEYIINWVKQRSGQGLEWIGW

FYPGSGDIKYNEKFKDKATLTADKSSSTVYMELSRLTSEDSAVYFCARNG

RWDDDYFDYWGQGTTVTVSS;

or
the variable light chain sequence (SEQ ID NO: 29)
DIQMTQSPSSLSAFVGGKVTITCKASQDIKKYIGWYQQKPGKGPRLLIHY

TSTLQPGIPSRFSGSGSGRDYSFSISNLEPEDIATYYCLQYDSLYTFGGG

TKLEIKR and the variable heavy chain sequence (SEQ ID NO: 30)
KVKLQESGAELMKPGASVKISCKSTGYTFSNYWIEWIKQRPGHGLEWIGE

ILPGSGSINYDEKFKGKATFTADTSSDTVYMFLSGLTSEDSAVYYCARQA

NRGFDSAWFAYWGQGTTVTVSS;

or
the variable light chain sequence (SEQ ID NO: 31)
DIELTQSHKFMSTSVGDRVSITCKASQDVTAAVAWYQQKPGQSPKLLIHS

ASYRYTGVPDRFTGSGSGSDFTFTISSVQAEDLAVYYCQQYYNTPLTFGA

GTKLELKR and the variable heavy chain sequence (SEQ ID NO: 32)
QVQLQESGPELVKPGASMKISCKASGYSFTEHIINWVKQTHRENLEWIGL

INPNSGGTNYNQKFKDKATLTVDTASNTAYMELLSLTSEDSAVYYCARLR

YDAAYWGQGTTVTVSS;

or a sequence substantially identical thereto.

A substantially identical sequence may comprise one or more conservative amino acid mutations. It is known in the art that one or more conservative amino acid mutations to a reference sequence may yield a mutant peptide with no substantial change in physiological, chemical, or functional properties compared to the reference sequence; in such a case, the reference and mutant sequences would be considered "substantially identical" polypeptides. Conservative amino acid mutation may include addition, deletion, or substitution of an amino acid; in one non-limiting example, the conservative amino acid mutation is a conservative amino acid substitution. A conservative amino acid substitution is defined herein as the substitution of an amino acid residue for another amino acid residue with similar chemical properties (e.g. size, charge, or polarity).

A conservative amino acid substitution may substitute a basic, neutral, hydrophobic, or acidic amino acid for another of the same group. By the term "basic amino acid" it is meant hydrophilic amino acids having a side chain pK value of greater than 7, which are typically positively charged at physiological pH. Basic amino acids include histidine (His or H), arginine (Arg or R), and lysine (Lys or K). By the term "neutral amino acid" (also "polar amino acid"), it is meant hydrophilic amino acids having a side chain that is uncharged at physiological pH, but which has at least one bond in which the pair of electrons shared in common by two atoms is held more closely by one of the atoms. Polar amino acids include serine (Ser or S), threonine (Thr or T), cysteine (Cys or C), tyrosine (Tyr or Y), asparagine (Asn or N), and glutamine (Gln or Q). The term "hydrophobic amino acid" (also "non-polar amino acid") is meant to include amino acids exhibiting a hydrophobicity of greater than zero according to the normalized consensus hydrophobicity scale of Eisenberg (1984). Hydrophobic amino acids include proline (Pro or P), isoleucine (Ile or I), phenylalanine (Phe or F), valine (Val or V), leucine (Leu or L), tryptophan (Trp or W), methionine (Met or M), alanine (Ala or A), and glycine (Gly or G). "Acidic amino acid" refers to hydrophilic amino acids having a side chain pK value of less than 7, which are typically negatively charged at physiological pH. Acidic amino acids include glutamate (Glu or E), and aspartate (Asp or D).

Sequence identity is used to evaluate the similarity of two sequences; it is determined by calculating the percent of residues that are the same when the two sequences are aligned for maximum correspondence between residue positions. Any known method may be used to calculate sequence identity; for example, computer software is available to calculate sequence identity. Without wishing to be limiting, sequence identity can be calculated by software such as NCBI BLAST2 service maintained by the Swiss Institute of Bioinformatics (and as found at http://ca.expasy.org/tools/blast/), BLAST-P, Blast-N, or FASTA-N, or any other appropriate software that is known in the art.

The substantially identical sequences of the present invention may be at least 85% identical; in another example, the substantially identical sequences may be at least 85, 86, 87, 88, 89, 90, 91, 92, 93, 94, 95, 96, 97, 98, 99, or 100% identical at the amino acid level to sequences described herein. Importantly, the substantially identical sequences retain the activity and specificity of the reference sequence. As would be known to one of skill in the art, amino acid residues of an antibody, particularly within the framework regions may be mutated (for example, by conservative substitution) without significantly affecting the functional properties of the antibody (antigen recognition and binding).

The isolated or purified antibody or fragment thereof of the present invention, and as described herein, may be specific to the ricin toxin lectin-B protein. The isolated or purified antibody or fragment thereof of the present invention may be an IgG.

The antibody or fragment thereof of the present invention also encompasses chimeric and humanized constructs based on the variable light chain or CDR sequences of the antibodies of the present invention. By the term "chimeric", it is meant that the variable light regions of the antibodies of the present invention, as described above, are grafted onto the constant regions (which may include $C_L$, $C_{H1}$, $C_{H2}$, and $C_{H3}$) from a different source. In one specific, non-limiting example, a chimeric construct may comprise the variable light regions of the present invention and human constant regions. Methods of preparing such chimeric constructs are well-known to those of skill in the art (Sun L K, 1987). By the term "humanized", it is meant that the CDR described above may be grafted onto the framework regions of human antibody fragments (Fv, scFv, Fab, sdAb). The humanized constructs may be prepared using any suitable method know in the art, for example, but not limited to humanization, CDR grafting, and veneering. Humanization of an antibody or antibody fragment comprises replacing an amino acid in the sequence with its human counterpart, as found in the human consensus sequence, without loss of antigen-binding ability or specificity; this approach reduces immunogenicity of the antibody or fragment thereof when introduced into human subjects. In the process of CDR grafting, one or more than one of the CDR defined herein may be fused or grafted to a human variable region ($V_H$, or $V_L$), or to other human antibody fragment framework regions (Fv, scFv, Fab). In such a case, the conformation of said one or more than one hypervariable loop is preserved, and the affinity and specificity of the sdAb for its target (i.e., ricin) is also preserved. CDR grafting is known in the art and is described in at least the following: U.S. Pat. Nos. 6,180,370, 5,693,761, 6,054,297, 5,859,205, and European Patent No. 626390. Veneering, also referred to in the art as "variable region resurfacing", involves humanizing solvent-exposed positions of the antibody or fragment; thus, buried non-humanized residues, which may be important for CDR conformation, are preserved while the potential for immunological reaction against solvent-exposed regions is minimized. Veneering is known in the art and is described in at least the following: U.S. Pat. Nos. 5,869,619, 5,766,886, 5,821,123, and European Patent No. 519596. Persons of skill in the art would be amply familiar with methods of preparing such humanized antibody fragments.

The antibody or fragment thereof of the present invention may also comprise additional sequences to aid in expression, detection, or purification of a recombinant antibody or fragment thereof. For example, and without wishing to be limiting, the antibody or fragment thereof may comprise a targeting or signal sequence (for example, but not limited to ompA), a detection tag (for example, but not limited to c-Myc, EQKLISEEDL, SEQ ID NO:33), a purification tag (for example, but not limited to a histidine purification tag, HHHHH, SEQ ID NO:34), or any combination thereof.

The antibody or fragment thereof of the present invention may also be in a multivalent display. Multimerization may be achieved by any suitable method of know in the art. For example, and without wishing to be limiting in any manner, multimerization may be achieved using self-assembly molecules (Zhang et al, 2004; Merritt & Hol, 1995), for example as described in WO2003/046560. The described method produces pentabodies by expressing a fusion protein comprising the antibody or fragment thereof of the present invention and the pentamerization domain of the B-subunit of an $AB_5$ toxin family (Nielson et al, 2000); the pentamerization domain assembles into a pentamer, through which a multivalent display of the antibody or fragment thereof is formed. Each subunit of the pentamer may be the same or different. Additionally, the pentamerization domain may be linked to the antibody or antibody fragment using a linker; such a linker should be of sufficient length and appropriate composition to provide flexible attachment of the two molecules, but should not hamper the antigen-binding properties of the antibody. In one non-limiting example, the linker may be the linker GPGGGSGGGGS (SEQ ID NO:35).

Other forms of multivalent display are also encompassed by the present invention. For example, and without wishing to be limiting, the antibody or fragment thereof may be presented as a dimer, a trimer, or any other suitable oligomer. This may be achieved by methods known in the art, for example direct linking connection (Nielsen et al, 2000), c-jun/Fos interaction (de Kruif et al, 1996), "Knob into holes" interaction (Ridgway et al, 1996).

The present invention also encompasses nucleic acid sequences encoding the molecules as described herein. The nucleic acid sequence may be codon-optimized. The present invention also encompasses vectors comprising the nucleic acids as just described.

The present invention additionally comprises hybridoma cells expressing the antibodies of the present invention. In a specific, non-limiting example, the present invention provides hybridoma cells A9, B10, D3 and D9, which express antibodies A9, B10, D3 and D9, respectively.

The present invention also provides a composition comprising one or more than one antibody or fragment thereof, as described herein. The composition may be a vaccine composition. In addition to the one or more than one antibody or fragment thereof, the composition may comprise a pharmaceutically acceptable diluent, excipient, or carrier. The diluent, excipient, or carrier may be any suitable diluent, excipient, or carrier known in the art, and must be compatible with other ingredients in the composition, with the method of delivery of the composition, and must not deleterious to the recipient of the composition. The one or more than one antibody or fragment thereof as described herein may also be formulated in a liposome or other form of encapsulation, using art-known methods. The liposome or encapsulation may optionally be formulated for timed-release; such formulations are well-known in the art.

The composition may be in any suitable form; for example, the composition may be provided in suspension form, powder form (for example, lyophilised), capsule or tablet form. For example, and without wishing to be limiting, when the composition is provided in suspension form, the carrier may comprise water, saline, a suitable buffer, or additives to improve solubility and/or stability; reconstitution to produce the suspension is effected in a buffer at a suitable pH to ensure the viability of the bacteria. In a specific, non-limiting example, the pharmaceutically acceptable carrier may be saline. Dry powders may also include additives to improve stability and/or carriers to increase bulk/volume; for example, and without wishing to be limiting, the dry powder composition may comprise sucrose or trehalose.

It would be within the competency of a person of skill in the art to prepare suitable compositions comprising the present compounds.

In yet another alternative, the one or more than one antibody or fragment thereof described herein may be delivered using a gene-therapy approach. For example, and without wishing to be limiting in any manner, the one or more than one antibody or fragment thereof may be encoded as a DNA vector within defective viruses (such as, but not limited to adenoviruses) for delivery into a subject's cell(s). Methods of delivering vaccines or therapeutics in this manner are well-known in the art (Fang J, et al, 2005).

The present invention further provides a method of preventing deleterious effects caused by ricin exposure or of treating exposure to ricin comprising administering one or more than one antibody or fragment thereof or a composition thereof as described herein to a subject in need thereof. The subject in need thereof may be any species of mammal that is susceptible to the effects of ricin; for example, and without wishing to be limiting in any manner, the mammal may be a mouse or a human.

When using the one or more than one antibody or fragment thereof for treatment of ricin exposure, the one or more than one antibody or fragment thereof may be administered to the subject up to several hours following exposure to the ricin toxin to rescue the subject from death. For example, the one or more than one antibody or fragment thereof may be administered 0, 0.5, 1, 1.5, 2.0, 2.5, 3.0, 3.5, 4.0, 4.5, 5.0, 5.5, 6.0, 6.5, 7.0, 7.5, or 8 hours following ricin exposure, or any time therebetween. In specific, non-limiting examples, a single antibody or fragment thereof as described herein may be administered to the subject between 0 and 4 hours following ricin exposure, while a synergistic combination of antibodies or fragments thereof may be administered between 0 and 8 hours following ricin exposure.

When using the one or more than one antibody or fragment thereof for preventing deleterious effects caused by ricin exposure (i.e. prophylaxis), the one or more than one antibody or fragment thereof may be administered to the subject up to several weeks prior to exposure to the ricin toxin. For example, the one or more than one antibody or fragment thereof may be administered 0, 0.5, 1, 1.5, 2.0, 2.5, 3.0, 3.5, 4.0, 4.5, 5.0, 5.5, 6.0, 6.5, 7.0, 7.5, 8.0, 8.5, or 9.0 weeks prior to ricin exposure, or any time therebetween to protect the subject against ricin exposure. In a specific, non-limiting example, a single antibody or fragment thereof, or a synergistic combination of antibodies or fragments thereof, as described herein may be administered to the subject between 0 and 9 weeks prior to ricin exposure.

As described above, more than one antibody or fragment thereof of the present invention may be combined to provide a synergistic effect with respect to the ricin-neutralizing activity. For example, and without wishing to be limiting in any manner, mAb D9 may be combined with any one or more of mAb A9, B10, and/or D3 to provide enhanced activity against ricin. In one specific example, mAb D9 and B10 may be combined for administration. Additionally, mAb D9 may be administered in combination with any prior art antibody to provide a similar synergistic effect; for example, and without wishing to be limiting in any manner, mAb D9 may be combined with mAb HRF4.

Yet another aspect of the present invention provides a method of conferring immunity against ricin comprising administering one or more than one antibody or fragment thereof as described herein, or a composition thereof. The one or more than one antibody or fragment thereof or composition comprising same may be administered by any suitable route know in the art. For example, and not wishing to be limiting, the one or more than one antibody or fragment thereof or composition comprising same may be administered subcutaneously, intramuscularly, orally, or by inhalation.

The present invention also provides a method of identifying hybridoma secreting effective anti-ricin antibodies, comprising:
a) providing hybridoma cells prepared from lymphocytes obtained from mice immunized against ricin;
b) exposing the cells to high amounts of ricin; and
c) identifying the cells that survive exposure step b).

In the method as described above, the mice from which the lymphocytes are obtained may have been immunized using stepwise increasing doses of ricin; the stepwise increasing doses may extend into the lethal range. This is contrary to methods commonly used in the art, where sublethal amounts of ricin, ricin toxoid or deglycosylated ricin in adjuvant are used. The hybridoma cells may be prepared from the fusion of lymphocytes, obtained from spleens taken from the immunized mice, and a myeloma cell line; this may be accomplished using any suitable method known in the art.

The hybridoma cells are then exposed to high amounts of ricin. The hybridoma cells may be isolated by dilution into individual containers (such as, but not limited to wells of a sterile microtitre plate) containing sterile cell culture medium. The high amount of ricin used in step b) of the method described above may be any suitable ricin final concentration; for example, and without wishing to be limiting in any manner, the final concentration of ricin may be in the range of 1 to 5 ng/ml; for example, the concentration of ricin may be 1, 1.5, 2, 2.5, 3, 3.5, 4, 4.5, or 5 ng/ml, or any concentration in the range as previously defined. In one specific, non-limiting example, the concentration of ricin may be 5 ng/ml. This amount of ricin represents a 25-fold increase in ricin over what has been used in the prior art (Furukawa-Stoffer et al, 1999); without wishing to be bound by theory, this may provide a more rigorous selection of antibody-secreting hybridoma, and allow selection of highly potent neutralizing antibodies.

The method described above may further comprise a step of confirming that the hybridoma of step c) survived ricin exposure by assessing secretion of effective anti-ricin antibodies. This step may be done by methods known in the art. The antibodies secreted by the hybridoma may be highly effective in neutralizing ricin.

The method as described above may also include a step of characterizing the antibody secreted by the hybridoma. The characterization may include identification of the antibody isotype, the antibody binding affinity and/or specificity to ricin (using for example, but not limited to ELISA assays or surface plasmon resonance), the antibody activity in in vitro (for example, but not limited to neutralization of ricin in a Vero cell culture) or in vivo (for example but not limited to neutralization of ricin in a mouse model).

Four hybridoma clones were developed and described herein that secreted high-titre anti-ricin IgG antibodies. These mAbs have great potential to be developed as antibody-based therapeutic agents or antibody-gene based vaccines against ricin. All four mAbs were found to have high ricin-neutralization potency both in an in vitro neutralization assay and an in vivo antibody/ricin co-incubation assay, indicating the strong inhibition of ricin-mediated cell death. Monoclonal antibody D9, found to be exceptionally active in the mouse assay, was further tested for post-exposure therapy and pre-exposure prophylaxis against ricin in vivo. It protected mice not only hours, but also several weeks (at least 6 weeks) before toxin challenge ($5 \times LD_{50}$ of ricin), and rescued mice up to 6 hours after poisoning ($5 \times LD_{50}$ of ricin); additionally, low amounts (0.5 µg) were therapeutic against high amounts of toxin (1 µg of ricin). Antibody D9 also showed synergistic effects with other anti-ricin mAb, as determined by the in vitro neutralization assay. A dose of 5 µg antibody in a mouse is equivalent to 1.4 mg in a human, which is in the lethal dose range. These results indicate that milligram amounts of specific anti-ricin monoclonal antibody in very small volumes (0.1 ml) may be sufficient to protect first responders or treat ricin-exposed casualties.

Ethical considerations prevent anti-ricin efficacy studies in humans; thus, evaluation of the antibodies or fragments thereof or compositions of the present invention must be conducted in animal models. The FDA has devised a policy, the Animal Rule (http://www.fda.gov/cber/rules/humeffic.htm; also see Federal Register: May 31, 2002 (Volume 67, Number 105, pages 37988-37998)), which permits approval of therapeutics or vaccines based on efficacy studies performed exclusively with animal models. The Animal Rule requires that any such animal models should mimic the human disease, and that therapeutic treatment or vaccine-elicited protection in animals should predict efficacy in humans. Based on the results in animal models presented herein and on the FDA's Animal Rule, the antibodies or fragments thereof or compositions of the present invention constitutes an excellent candidate as an anti-ricin vaccine for both animals and humans.

The present invention will be further illustrated in the following examples. However, it is to be understood that these examples are for illustrative purposes only and should not be used to limit the scope of the present invention in any manner.

EXAMPLE 1

Preparation of Ricin Stock

Because ricin is a possible terrorist biothreat, it is very difficult to obtain from commercial sources. Castor beans were obtained and working stocks of ricin were prepared. Specifics regarding the source of castor beans and preparation of the ricin stock cannot be disclosed due to security issues.

Ricin was prepared from castor bean seeds in Defence Research and Development Canada-Suffield. The toxicity of ricin stock was also determined. One LD50 of ricin for mice was determined by the i.p. injection of a series of ricin dilution into mice. The mice were observed for 7 days. The amount of ricin for 1×LD50 delivered by the i.p. route for one 20-25 gram female Balb/c mouse was 0.215 µg; 5×LD50 was 1.075 µg, or about 1 µg. For 5×LD50 of ricin delivered by the i.p. route, mice died within 1-2 days.

EXAMPLE 2

Creation and Selection of Hybridoma

Mice were used to obtain antibody hybridoma. The mice are kept in a secure BSL-2 area, cared for under the Canadian Council on Animal Care (CCAC) guidelines, and assessed for alternative endpoints.

Groups of 5 BALB/c female mice were injected i.p. with increasing amounts of ricin (0.2, 1.0, 5 and 25×$LD_{50}$) from Example 1 in 0.1 ml sterile 0.9% saline per mouse. Depending on their recovery (weight gain, a lack of illness symptoms), injections of increasing ricin amounts were 2-3 weeks apart. Two weeks after the final dose, the mice were bled by nicking the tail vein with a scalpel while the mouse was in a restraint chamber; blood was collected into a sterile micro centrifuge tube and allowed to clot at room temperature for 30 min. The sample was then centrifuging at 2300×g for 5 min and the serum was collected; if required, the serum was stored at −20° C. until needed.

ELISA was performed to determine anti-ricin IgG antibody titres. Ninety-six-well ELISA plates (Nunc Maxisorp, Canadian Life Technologies, Burlington, ON) were coated with 100 µl per well of 5 µg/ml ricin in carbonate bicarbonate buffer, pH 9.6, then incubated overnight at 4° C. After blocking with dilute BSA, the plates were incubated with 100 µl of serum dilutions for 2 hr at room temperature. Anti-ricin antibodies were detected by incubation with 1:3000 diluted HRP-goat anti-mouse IgG (Caltag Laboratories, Burlingame, Calif.) followed by the addition of a tetramethylbenzidine peroxidase substrate (Kirkegaard and Perry Laboratories, Gathersburg, Md.). Absorbance was measured at 615 nm by a microplate autoreader (Molecular Devices, Sunnyvale, Calif.).

The two mice with the highest titres were sacrificed three days after the last booster to collect lymphocytes. These mice were sacrificed by cervical dislocation then the abdomen was swabbed with 70% ethanol and opened with sterile scissor and forceps. Spleens were aseptically dissected from the immunized mice and were ground gently with autoclaved frosted-glass slides in Dulbecco's Modified Eagle's Medium (DMEM; Invitrogen) then filtered through a wire mesh screen to prepare splenocytes. Hybridomas were produced by fusing the splenocytes with Sp 2/0 myeloma cells (ATCC accession number CRL-1581, ATCC, Rockville, Md.) using a Clonacell™-HY Kit (StemCell Technologies, Vancouver, BC), following the manufacturer's instruction and growing these in semisolid medium with 2.5 ng/ml ricin (10×hybridoma cell culture lethal dose). After 2 weeks, single hybridoma clones were picked up from semisolid medium, transferred to 96-well tissue culture plates and then grown for 1 week in Clonacell Medium E with 5 ng/ml ricin (20×hybridoma cell culture lethal dose) for further selection.

From the surviving clones, the supernatant was removed and assessed by ELISA (as described above) for anti-ricin antibodies. The antibodies were further characterized using a mouse IsoStrip Kit from Roche Diagnostics (Laval, QC) following the manufacturer's instruction. Only clones expressing IgG antibodies were further used. Twenty-five clones survived this high concentration of toxin and from these, a panel of 4 hybridoma clones (A9, B10, D3, D9) with high specific reactivity for ricin were identified by ELISA.

EXAMPLE 3

Antibody Purification and Characterization

The four hybridoma clones of Example 2 were cultured and the expressed antibodies were purified and characterized.

Hybridoma clones A9, B10, D3, and D9 were separately cultured in DMEM supplemented with 10% FBS. Monoclonal antibodies (mAb) were purified from the cell culture supernatants by Melon Gel purification (Melon Gel Monoclonal IgG Purification Kit, Pierce, Rockford, Ill.) according to the manufacturer's protocol. The supernatant was dialyzed for two 1 hr exchanges in Melon Gel IgG Purification Buffer pH 7.0 and was loaded onto a column containing the Melon Gel resin. After 5 minute incubation with end-over-end mixing, the purified IgG was collected in the flow-through fraction. All IgG purified samples were aliquoted and stored at minus 20° C. The purity of the mAb was 85-90%, as assessed by SDS-PAGE (data not shown).

The purified mAb were also isotyped using a mouse IsoStrip™ Kit. All the mAb showed the same subtype of heavy chain, gamma 1, and the same type of light chain, kappa. The immunoreactivities of these mAb to the ricin were investigated by ELISA. All the mAb bound to ricin (FIG. 1) in a dose-dependent manner. HRF4 (Furukawa-Stoffer, T. L., 1999) was used as a positive control, showing high activity. Particularly interesting is the average activity shown by D9 antibody.

Four anti-ricin neutralizing antibody variable sequences were determined using PCR with degenerate primers specific for mouse antibodies (Amersham Pharmacia). Briefly, total RNA was isolated from hybridoma cell lines (Qiagen RNeasy Plus Mini) and reverse-transcribed with Superscript II RNase (Invitrogen) and an oligo dT primer (12-18 mer) to produce cDNA. Platinum Taq DNA Polymerase High Fidelity (Invitrogen) was used to amplify the ScFv genes, $V_H$ and $V_L$ with degenerate primers (Amersham Pharmacia Biotech) for PCR (Eppendorf Mastercyler gradient). Distinct bands of about 340 bp for $V_H$ and about 325 bp for $V_L$ were detected on a 1.5% agarose gel after PCR and the bands were purified (Qiagen Gel Extraction) and cloned into Zero Blunt TOPO PCR cloning vector (Invitrogen) for sequencing (Beckman Coulter CEQ 8000 Genetic Analyzer).

The amino acid sequences for the variable domains of mAb A9, B10, D3, and D9 are shown below, with CDR regions underlined.

A9 variable light chain
(SEQ ID NO: 25)
DIQMTQSPSSLSASLGGKVTITC<u>KASQDIKQYIA</u>WYQYKPGKGPRLLIH<u>Y
TSTLQPG</u>IPSRFSGSGSGRDYSFSISNLDPEDIATYYC<u>LQYDHLYT</u>FGGG
TKLEIKR A9 variable heavy chain
(SEQ ID NO: 26)
KVQLQESGAELMKPGASVKISCKATGYTFS<u>SYWIQ</u>WIKQRPGHGLEWIG<u>E
ILPGTGNTNYSEKFKG</u>KATFTTDTSSNTAYMHFSSLTSEDSAVYYCSR<u>CE
GEGYFQAWFAY</u>WGQGTTVTVSS B10 variable light chain
(SEQ ID NO: 27)
DIVLTQSPSSMYASLGERVTITC<u>KASQDINNYLRW</u>FQQKPGKSPKTLIY<u>R
ANRLVDG</u>VPSRFSGSGSGQDYSLTISSLEYEDMGFYSC<u>LQYDEFPYT</u>FGG
GTKLEIKR B10 variable heavy chain
(SEQ ID NO: 28)
EVQLQESGTGLVKPGASVKLSCKASGYTFT<u>EYIIN</u>VVVKQRSGQGLEWIG
<u>WFYPGSGDIKYNEKFKD</u>KATLTADKSSSTVYMELSRLTSEDSAVYFCAR<u>N
GRWDDDYFDY</u>WGQGTTVTVSS D3 variable light chain
(SEQ ID NO: 29)
DIQMTQSPSSLSAFVGGKVTITC<u>KASQDIKKYIG</u>WYQQKPGKGPRLLIH<u>Y
TSTLQPG</u>IPSRFSGSGSGRDYSFSISNLEPEDIATYYC<u>LQYDSLYT</u>FGGG
TKLEIKR D3 variable heavy chain
(SEQ ID NO: 30)
KVKLQESGAELMKPGASVKISCKSTGYTFS<u>NYWIE</u>WIKQRPGHGLEWIG<u>E
ILPGSGSINYDEKFKG</u>KATFTADTSSDTVYMFLSGLTSEDSAVYYCAR<u>QA
NRGFDSAWFAY</u>WGQGTTVTVSS D9 variable light chain
(SEQ ID NO: 31)
DIELTQSHKFMSTSVGDRVSITC<u>KASQDVTAAVA</u>WYQQKPGQSPKLLIH<u>S
ASYRYT</u>GVPDRFTGSGSGSDFTFTISSVQAEDLAVYYC<u>QQYYNTPLT</u>FGA
GTKLELKR D9 variable heavy chain
(SEQ ID NO: 32)
QVQLQESGPELVKPGASMKISCKASGYSFT<u>EHIIN</u>WVKQTHRENLEWIG<u>L
INPNSGGTNYNQKFKD</u>KATLTVDTASNTAYMELLSLTSEDSAVYYCAR<u>LR
YDAAY</u>WGQGTTVTVSS To determine the general specificity of the antibodies, immunoblots were performed as follows. Ricin, ricin A-chain and ricin B-chain were separated by 10% SDS-PAGE in an X-Cell Sure Lock Mini-Cell apparatus (Invitrogen). The separated proteins were electrophoretically transferred onto PVDF membranes (Millipore Corp. Bedford, Ma) using Mini Trans-Blot system (Bio-Rad Laboratories) with MOPS buffer (50 mM MOPS, 50 mM Tris-base, 0.1% SDS, 1 mM EDTA, pH 7.7, and 10% methanol). Membranes were blocked with Superblock buffer (Fisher Scientific Company, Canada), followed by 3× washing for 5 min each with PBS containing 0.05% tween-20 (PBST). The membranes were then incubated with anti-ricin antibodies 1:1000 dilution in Superblock buffer overnight at 4° C. Following 3 washes with PBST, the membranes were incubated with IgG-HRP conjugated rabbit anti-mouse antibody (Jackson ImmunoResearch Laboratories) 1:3000 dilution in Superblock buffer at room temperature for 1 hr, followed by 3 washes with PBST. The specific binding was detected with ECL kit (Amersham Biosciences) and imaged using VersaDoc™ 5000 system (Bio-Rad Laboratories).

Figure 2:
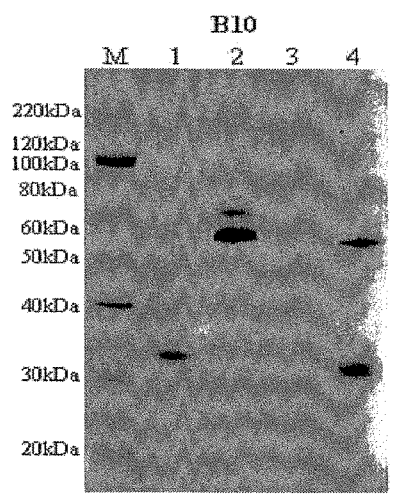
FIG. 2 is a Western blot of monoclonal antibody B10 against ricin to determine the general specificity of the antibody. Lane 1—ricin in reducing conditions (2.2 µg/lane); Lane 2—ricin (1.1 µg/lane); Lane 3—ricin A chain (0.4 µg/lane); Lane 4—ricin B chain (0.4 µg/lane); M—molecular weight markers.
Figure 3:
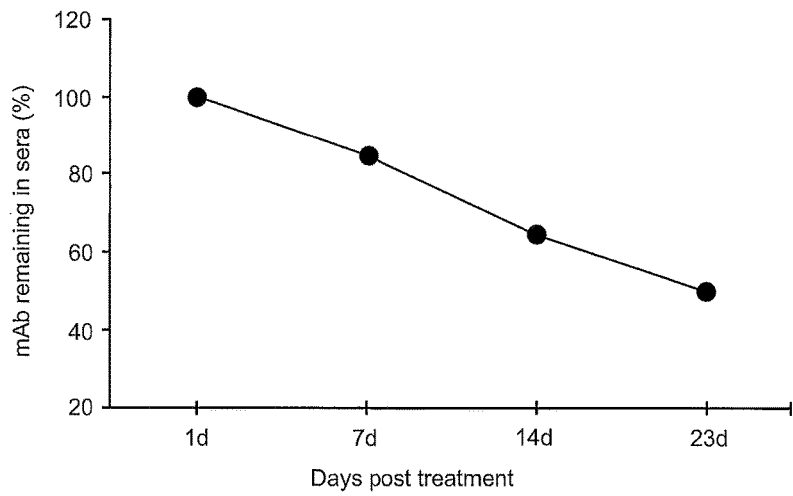
FIG. 3 is a graph depicting the half-life of D9 in mouse serum. D9 at the dose of 5 μg was administered by the i.p. route into mice. Mice were sacrificed at different time points to calculate plasma concentration of D9 using an immunoassay. The D9 remaining in sera is expressed as percentages plotted against time in days on the figure.

In the SDS-PAGE process above, ricin was disassociated into the higher molecular weight B-chain and lower molecular weight A-chain. All of the mAb (A9, B10, D3, and D9) specifically bound to the B-chain. Results for B10, representative of other antibodies, are shown in FIG. 2. As shown, B10 binds to whole ricin (lanes 2) and B-chain (lane 4) but not A-chain (lane 3). All of the present mAb bound to the B-chain, blocked its ability to bind to cell membranes, and so prevented the toxic A-chain from entering and killing the cell. This is in contrast to existing antibodies, where most therapeutic candidates are monoclonal antibodies with binding activity against the toxic A-chain. This is a logical course, as one skilled in the art would seek an antibody that would neutralize the toxic part of ricin for effective therapy.

EXAMPLE 4

In vitro Neutralization Assay

An in vitro neutralization assay involving co-incubation of antibody and toxin followed by administration to cell culture was used to assess the activity of the IgG of Example 3.

The amount of antibody was determined by an Easy-Titer Mouse IgG Assay Kit (Easy-Titer Mouse IgG Assay Kit, Pierce, Rockford, Ill.) according to the manufacturer's protocol. In a microtitre plate, 20 µl of anti-IgG sensitized beads followed by 20 µl of the IgG under investigation was added to each well followed by mixing for 5 minutes at room temperature. The plate was then blocked with 100 µl Blocking Buffer for 5 min with mixing and read at an absorbance of 405 nm by a microplate autoreader (Molecular Devices). The antibody concentrations were 4.8 mg/ml for A9, 0.68 mg/ml for B10, 1.96 mg/ml for D3 and 1.15 mg/ml for D9.

To determine the activity of a given antibody, it was first diluted in culture media to 10 µg/ml. 200 µl of the diluted antibody was added to the first well in a microtitre plate column, and 100 µL of culture medium was added to the other wells of that column. 100 µL was transferred to the next well in the column to make a 2-fold dilution, this was continued and the last well in the column had 100 µL removed so that all wells had 100 µL of serially diluted antibody. Ricin was diluted in culture media to 300 ng/ml and 50 µL ricin was added to each well; the plate was incubated with 5% $CO_2$ at 37° C. for 2 hours.

Vero cells were maintained in DMEM with 10% FBS (fetal bovine serum) in 75 $cm^2$ Falcon culture flasks with 5% $CO_2$ at 37° C., with medium renewal every 2-3 days. When cells were 60-80% confluent, trypsin was used to detach the cells, and the concentration of cells was estimated by counting these with a hemocytometer. The cells were diluted to $2\times10^5$ cells/ml and 50 μl of the cell suspension was added to each well in the above microtitre plate following the 2-hour incubation of ricin and antibody. The plate was incubated with 5% $CO_2$ at 37° C. for 2 days.

Following incubation, 20 μL of Alamar Blue (TREK Diagnostic System, Ohio) was added to each well and the plate was incubated with 5% $CO_2$ at 37° C. for 5-6 hours. On a plate reader (Molecular Devices), the plate was read at absorbances of 570 nm and 600 nm, readings were normalized by subtracting the absorbance reading of wells that did not have cells, and the data point was the average of $A_{570nm}+A_{600nm}$ of triplicate wells. As would be known to one of skill in the art, Amalar dye diffuses into dead cells and gives these a high absorbance at 600 nm; if the cells are viable, they will secrete the dye and oxidize Alamar Blue, giving a reduced 600 nm reading and an increased 570 nm reading. When dividing $A_{570nm}$ by the $A_{600nm}$, larger numbers indicate higher viability of the cells. A standard curve was plotted using readings for wells in the absence of ricin (100% viability), high amounts of ricin and no antibodies (0% survival), and variable amounts of ricin.

The standard curve was used to assess viability of cells in the test wells (ricin co-incubated with mAb). Viability results less than 100% (e.g. 49%) indicate that cells in the test wells (ricin+mAb) were viable but stopped growing, resulting in low readings compared to control cells that continued to grow. Results are shown in Table 1, where it appeared that B10 mAb performed best in neutralizing ricin in this in vitro assay.

TABLE 1

Relative number of cells surviving 75 ng ricin/mL co-incubated with mAb.

| mAb concentration | Viable cells (% of control cells) given 75 ng/ml ricin + mAbs | | | | |
|---|---|---|---|---|---|
| (ng/mL) | A9 | B10 | D3 | D9 | HRF4 |
| 5000 | 65 | 77 | 60 | 106 | 46 |
| 1700 | 79 | 68 | 40 | 49 | 24 |
| 560 | 51 | 49 | 33 | 24 | 20 |
| 190 | 24 | 49 | 21 | 19 | 13 |
| 62 | 7 | 22 | 14 | 14 | 9 |
| 21 | 9 | 10 | 9 | 15 | 7 |
| 6.9 | 8 | 6 | 7 | 6 | 5 |
| 2.3 | 8 | 7 | 4 | 8 | 7 |

EXAMPLE 5

In vivo Neutralization Assay

An in vivo neutralization assay involving antibody administration with ricin to mice was used to assess the activity of the IgG of Example 3.

Briefly, different amounts of antibody (from 0.4 to 10 μg/mouse) were co-incubated with $5\times LD_{50}$ of ricin (1 hr, 37° C., with gentle inversion mixing every 15 min); the mixture was then injected intraperitoneally (i.p.) into BALB/c female mice. Two antibody gold-standards were used as controls: polyclonal goat anti-ricin IgG antibody and mouse mAb HRF4. Results are as shown in Table 2.

TABLE 2

Survival of mice given $5 \times LD_{50}$ of ricin co-incubated with varying amounts of antibody. The number of viable mice on each day following administration is given.

| Antibody | Amount (μg) | Day 1 (number) | Day 2 | Day 3 | Day 4 | Day 5 | Day 6 | Day 7 | Day 11 |
|---|---|---|---|---|---|---|---|---|---|
| Control | 0 | 3 | 0 | — | — | — | — | — | — |
| Purified | 20 | 3 | 3 | 3 | 3 | 3 | 3 | 3 | 3 |
| Goat Ab | 4 | 3 | 1 | 0 | — | — | — | — | — |
| | 0.8 | 3 | 0 | — | — | — | — | — | — |
| HRF4 | 10 | 3 | 3 | 2 | 2 | 1 | 0 | — | — |
| | 2 | 3 | 0 | — | — | — | — | — | — |
| | 0.5 | 5 | 1 | 0 | — | — | — | — | — |
| | 0.4 | 2 | 0 | — | — | — | — | — | — |
| A9 | 10 | 3 | 3 | 3 | 3 | 3 | 3 | 3 | 3 |
| | 2 | 3 | 3 | 3 | 3 | 3 | 3 | 3 | 3 |
| | 0.5 | 5 | 1 | 0 | — | — | — | — | — |
| | 0.4 | 3 | 1 | 0 | — | — | — | — | — |
| B10 | 10 | 3 | 3 | 3 | 3 | 3 | 3 | 3 | 3 |
| | 2 | 3 | 3 | 3 | 3 | 3 | 3 | 3 | 3 |
| | 0.5 | 5 | 5 | 4 | 0 | — | — | — | — |
| | 0.4 | 3 | 1 | 0 | — | — | — | — | — |
| D3 | 10 | 3 | 3 | 3 | 3 | 3 | 3 | 3 | 3 |
| | 2 | 3 | 3 | 3 | 3 | 1 | 1 | 1 | 1 |
| | 0.5 | 5 | 5 | 3 | 0 | — | — | — | — |
| | 0.4 | 3 | 3 | 0 | — | — | — | — | — |
| D9 | 10 | 3 | 3 | 3 | 3 | 3 | 3 | 3 | 3 |
| | 2 | 3 | 3 | 3 | 3 | 3 | 3 | 3 | 3 |
| | 0.5 | 5 | 5 | 5 | 5 | 5 | 5 | 5 | 5 |
| | 0.4 | 3 | 3 | 3 | 1 | 0 | — | — | — |

In in vitro assays, mAb HRF4 was the best binding mAb in ELISA studies (Example 3) and B10 was the best neutralizing antibody in the cell culture assay (Example 4). However, in both in vitro assays, mAb D9 appeared unexceptional. Only in the present in vivo mouse model assessment did D9 show itself to have exceptional merit as a medical countermeasure against ricin. Thus, the results of in vitro analysis are not necessarily indicative of in vivo efficacy of anti-ricin mAb. Surprisingly, 0.5 μg of D9 antibody was effective in protecting mice from 5×$LD_{50}$ (1 μg ricin). At this level of efficacy, mAb D9 surpasses the activity of all other antibodies reported to date.

It is worth noting that all antibodies of the present invention out-performed the previous gold standard monoclonal antibody, HRF4, as well as the goat anti-ricin polyclonal antibodies.

EXAMPLE 6

Efficacy of Antibody Given Before or after Ricin Exposure

Existing publications suggest ricin enters a mammalian cell after only about 30 minutes, and that not much can be done to rescue a casualty or animal beyond this time. Also, current literature suggests anti-ricin antibodies can be administered hours to a few days before ricin poisoning to protect mice. In this Example, the survival of mice administered the antibodies of Example 3 at various time-points prior to or following ricin exposure is assessed.

Antibody administration following ricin exposure: The mice were assessed using the in vivo neutralization assay as described in Example 5, except that 5 μg of antibody (A9, B10, D3, D9, HRF4 (positive control)) was administered 1, 2, 4, or 6 hours following ricin exposure, or saline was administered at 1 hour following ricin exposure (negative control). Each experimental group comprised 4 mice. Results are shown in Table 3.

TABLE 3

Survival of mice administered antibody at varying time-points after receiving 5 × $LD_{50}$ of ricin. The number of viable mice on each day following administration of antibody is given.

| | Time points | Day 1 | Day 2 | Day 3 | Day 4 | Day 5 | Day 6 | Day 7 |
|---|---|---|---|---|---|---|---|---|
| Control | 1 hr | 4 | 1 | 0 | — | — | — | — |
| HRF4 | 1 hr | 4 | 2 | 0 | — | — | — | — |
| 5 μg per | 2 hr | 3 | 1 | 0 | — | — | — | — |
| mouse | 4 hr | 4 | 2 | 0 | — | — | — | — |
| | 6 hr | 3 | 0 | — | — | — | — | — |
| A9 | 1 hr | 4 | 4 | 4 | 4 | 4 | 4 | 4 |
| 5 μg per | 2 hr | 4 | 4 | 2 | 2 | 0 | — | — |
| mouse | 4 hr | 4 | 4 | 3 | 2 | 0 | — | — |
| | 6 hr | 4 | 3 | 1 | 1 | 0 | — | — |
| B10 | 1 hr | 4 | 4 | 4 | 4 | 4 | 4 | 4 |
| 5 μg per | 2 hr | 4 | 4 | 4 | 4 | 4 | 4 | 4 |
| mouse | 4 hr | 4 | 4 | 4 | 2 | 2 | 2 | 2 |
| | 6 hr | 4 | 3 | 3 | 0 | — | — | — |
| D3 | 1 hr | 4 | 3 | 3 | 3 | 3 | 3 | 3 |
| 5 μg per | 2 hr | 4 | 4 | 4 | 4 | 2 | 2 | 2 |
| mouse | 4 hr | 4 | 4 | 2 | 2 | 0 | — | — |
| | 6 hr | 4 | 4 | 2 | 0 | — | — | — |
| D9 | 1 hr | 4 | 4 | 4 | 4 | 4 | 4 | 4 |
| 5 μg per | 2 hr | 4 | 4 | 4 | 4 | 4 | 4 | 4 |
| mouse | 4 hr | 4 | 4 | 4 | 4 | 4 | 4 | 4 |
| | 6 hr | 4 | 4 | 4 | 4 | 4 | 4 | 4 |
| | 8 hr | 3 | 2 | 0 | — | — | — | — |

All antibodies of the present invention were capable of rescuing mice when antibody was administered 1-2 hours following ricin exposure. In fact, and as in Example 5, the present antibodies out-performed both HRF4 and the goat polyclonal antibodies. Table 3 shows conclusively that antibodies, especially D9, can be given several hours after ricin poisoning to rescue mice.

Antibody administration prior to ricin exposure: Due to superiority of the D9 antibody and to reduce the amount of animals required for experimentation, this portion of testing was done using only D9 mAb. The mice were assessed using the in vivo neutralization assay as described in Example 5, except that 5 μg D9 mAb was administered 1, 7, 14, 28, or 42 days prior to ricin exposure, or no antibody was administered prior to ricin exposure (negative control). Each experimental group comprised 4 mice. Results are shown in Table 4.

TABLE 4

Survival of mice administered D9 mAb at varying time-points prior to receiving 5 × $LD_{50}$ of ricin. The number of surviving mice 7 days following administration of ricin is given.

| | Time point | Survival |
|---|---|---|
| Negative control | | 0 * |
| D9 | 1 day | 4 (100%) |
| | 7 days | 4 (100%) |
| | 14 days | 4 (100%) |
| | 28 days | 4 (100%) |
| | 42 days | 4 (100%) |

* all died or had to be terminated after 1 day

Table 4 shows that, aside from some minor temporary weight loss (data not shown), no deaths were observed when D9 antibody was given 1, 7, 14, 28 or 42 days before mice were administered 5×$LD_{50}$ of ricin. Based on previous results, it can be hypothesized that mAb A9, B10, and D3 would be similarly, if only slightly less, effective.

Given that there is some clearance or turnover with time, the question of the amount of time necessary for the 5 μg of administered antibody to attain levels below the protective amount of 0.5 μg antibody (determined in Example 5) within the mouse was addressed. To conserve on the use of mice, an extrapolation was done by assessing the amount of D9 antibody in mouse blood over different time points. Mice were given 5 μg of D9 antibody each, and each week a group of mice was bled via that tail vein (see Example 2), the sera collected and the amount of D9 antibody in that sera assessed by ELISA quantitation (see Example 2). Results are shown in FIG. 3, where the half life of the anti-ricin D9 antibody was estimated at 18.5 days in the mice. From this data, it can be extrapolated that after 6 weeks the amount of D9 per mouse would be about 1 μg, above the 0.5 μg minimum. This large window for protection is understandable given that D9 is a mouse antibody circulating within mice. A humanized anti-ricin monoclonal antibody based on the antibodies of the present invention, circulating in a human, may have a similarly long half-life.

It is difficult to compare efficacy of different anti-ricin antibodies previously reported in the literature using different experimental settings, such as different antibody administration routes, different animal models, and so on. However, two reports appear to have experiment settings were similar to the present Examples. One report showed that anti-ricin antibody CD12 or R70, at the dose of 5, 10, 20, or 40 μg/mouse could protect mice against 5×$LD_{50}$ of ricin challenge when the antibody was administered 24 h before ricin challenge (Neal L M, et al, 2010). The second report showed that 100 µg/mouse anti-ricin antibody 4C13 could rescue mice 30 minutes after ricin challenge (10×LD$_{50}$; Guo J, et al, 2006). In contrast, the present Examples show that administration of 5 µg/mouse of D9 antibodycan protect mice for at least 6 weeks before ricin challenge (5×LD50) or can rescue mice 6 hours after ricin challenge (5×LD50).

EXAMPLE 7

Synergistic Effect of D9 mAb

Combinations of the antibodies of Example 3 were assessed to assess the presence of synergistic activities.

Figure 4:
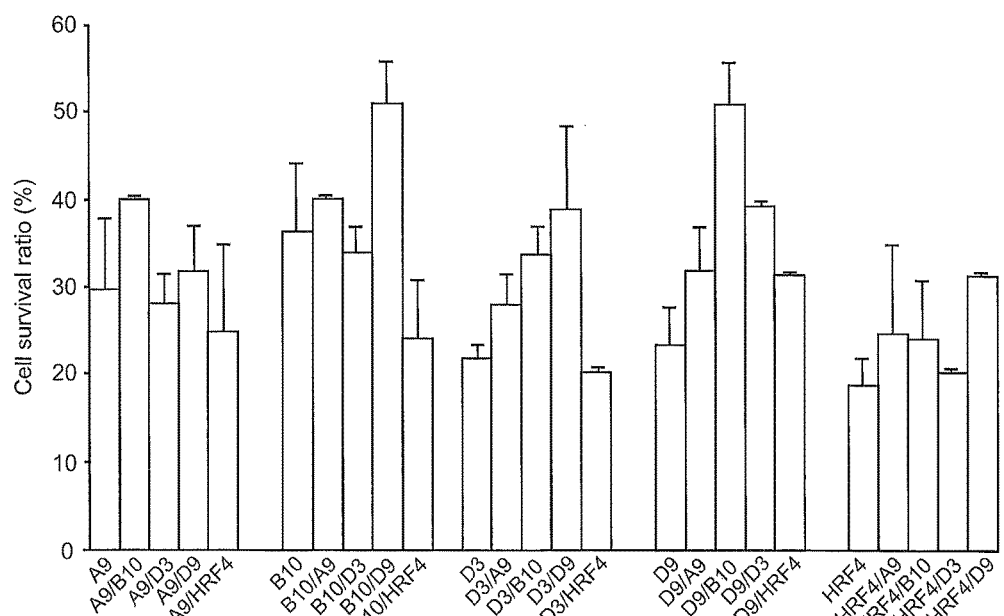
FIG. 4 is a bar graph depicting the effect of combining mAb of the present invention. Antibodies were mixed at a 1:1 ratio (total concentration 313 ng/ml) and assayed in vitro using Amalar Blue dye. A synergistic effect was noted when mAb D9 was combined with other antibodies of the present invention.

The mice were assessed using the in vitro neutralization assay as described in Example 4, except that 1:1 ratio mixtures of antibody (A9, B10, D3, D9, HRF4) were used, at a total concentration of 313 ng/ml. Antibody alone was also used, at a concentration of 156 ng/ml. Results are shown in FIG. 4.

A very large set of data was generated but in summation, no matter which antibody was used, D9 had a helper effect, especially for B10. If the effect of the antibody combination was simply additive, the results for the antibody alone and the combination should be equivalent. FIG. 4 shows that the values for cell survival were far higher when D9 was added to any of the other mAb.

To evaluate the synergistic effect in vivo, the effect of administering the combination of D9 and B10 at various time-points following ricin exposure was assessed. This was performed according to the method described in Example 6, except that 0.5 µg of D9 mAb and 0.5 µg of B10 mAb, or 5 µg of D9 mAb and 5 µg of B10 mAb. Synergism was further observed when either 0.5 µg of D9 mAb and 0.5 µg of B10 mAb, 5 µg of D9 mAb and 5 µg of B10 mAb, or saline were administered to mice 8 hours after ricin poisoning (n=4, each group). Results are shown in Table 5.

In Example 6, the best candidate, D9 mAb, did not differ from saline controls when given 8 hours after ricin poisoning (Table 3); if the combination of D9 and B10 had any synergistic additional effect, it would be seen at this time point. The present results (Table 5) showed that the combination of antibodies either prevented death or extended the time of death. Specifically, 1 of 4 mice survived when administered 0.5 µg each D9 and B10, while life was extended a few days for mice administered 5 µg each D9 and B10. The extended time to death is encouraging, as it may open a window of opportunity for casualties to receive supportive care and increased survival following ricin exposure.

TABLE 5

Survival of mice that administered mAb therapy 8 hours following administration of 5 × LD$_{50}$ of ricin. The number of viable mice on each day following administration of antibody is given.

| | Number of surviving mice from a group of 4 | | | | | | |
|---|---|---|---|---|---|---|---|
| | Day 1 | Day 2 | Day 3 | Day 4 | Day 5 | Day 6 | Day 7 |
| Ricin + saline | 4 | 0 | — | — | — | — | — |
| 0.5 µg of D9 mAb + 0.5 µg of B10 mAb | 4 | 2 | 1 | 1 | 1 | 1 | 1 |
| 5 µg of D9 mAb + 5 µg of B10 mAb | 4 | 4 | 3 | 2 | 0 | — | — |

EXAMPLE 8

Chimeric Construct of Anti-ricin Antibodies

Chimeric constructs of antibodies of Example 3 were prepared. Here, the term "chimeric" is used to define an antibody where the mouse antibody's constant region is replaced with a human constant region.

Briefly, variable regions of heavy and light chains for B10 and D9 were grafted onto human gamma 1 heavy chain constant region and kappa 1 light chain constant region, respectively, to assemble the whole chimeric antibody genes, resulting in chimeric B10 and D9.

The chimeric antibody DNA sequence (2 kb) was synthesized as follows. A light chain leader sequence was upstream from the light chain, followed by a foot-and-mouth disease virus 2A self-cleavage linker encoding APVKQTL-NFDLLKLAGDVESNPGP (SEQ ID NO: 36) before the heavy chain. The whole DNA sequence flanked by Kpn I and Hind III was synthesized by GenScript Corporation (Scotch Plaines, N.J.) and cloned into pUC57 vector, resulting in pUC57-chimeric B10 or D9. A recombinant adenovirus vector expressing chimeric B10 or chimeric D9 was constructed using AdEasy system (Qbiogene, Carlsbad, Calif.) according to the manufacturers protocol. Briefly, Kpn I-Hind III fragment of pUC57-chimeric B10 or pUC57-chimeric D9 was ligated to a Kpn I-Hind III-digested pShuttle-CMV vector. The resulting pShuttle construct was co-transformed with the pAdEasy-1 vector into E. coli BJ5183 cells to produce recombinant adenoviral genomic construct for hu1A4A1IgG1 protein. The recombinant adenoviral construct, pAd-chimeric B10 or D9 was linearized with Pac I and transfected into HEK 293 cells (ATCC) cultured in Dulbecco's Modified Eagle's Medium supplemented with 5% fetal bovine serum (FBS) for amplification and then the amplified adenovirus was purified by a chromatographic method.

To express chimeric B10 or chimeric D9, HEK 293 cells were infected with the recombinant adenovirus pAd-chimeric B10 or pAd-chimeric D9 at a multiplicity of infection of 1. The infected cells were cultured for one week and the culture supernatant was harvested. The expressed chimeric B10 or chimeric D9 was purified using protein L agarose gel from Pierce Biotechnology (Rockford, Ill.). Briefly, culture supernatant was dialyzed against phosphate buffer saline (PBS) (Sigma-Aldrich) for 12 hr then concentrated using PEG (Sigma-Aldrich) to less than 50 ml. The concentrated sample was incubated with 2 ml protein L agarose gel at 4° C. for 1 hr. The gel and supernatant mixture was then loaded onto an empty column, which was subsequently washed with binding buffer. Bound chimeric B10 or chimeric D9 was eluted with elution buffer. The eluted Ab was further desalted using excellulose column (Pierce Biotechnology) then concentrated by Centricon YM-30 (Millipore Corp., Bedford, Mass.).

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

EXAMPLE 9

Humanization of Antibodies

Molecular Modeling and Structural Analysis of D9 Fv

Different approaches have been developed to humanize murine antibodies in order to reduce the antigenicity of murine antibodies in humans. Despite the development of molecular display technologies and transgenic animals for the generation of fully human antibodies, CDR grafting to transfer all murine antibody CDRs onto the human antibody FRs remains an attractive and proven strategy for overcoming therapeutic deficiencies of murine antibodies.

Figure 5:
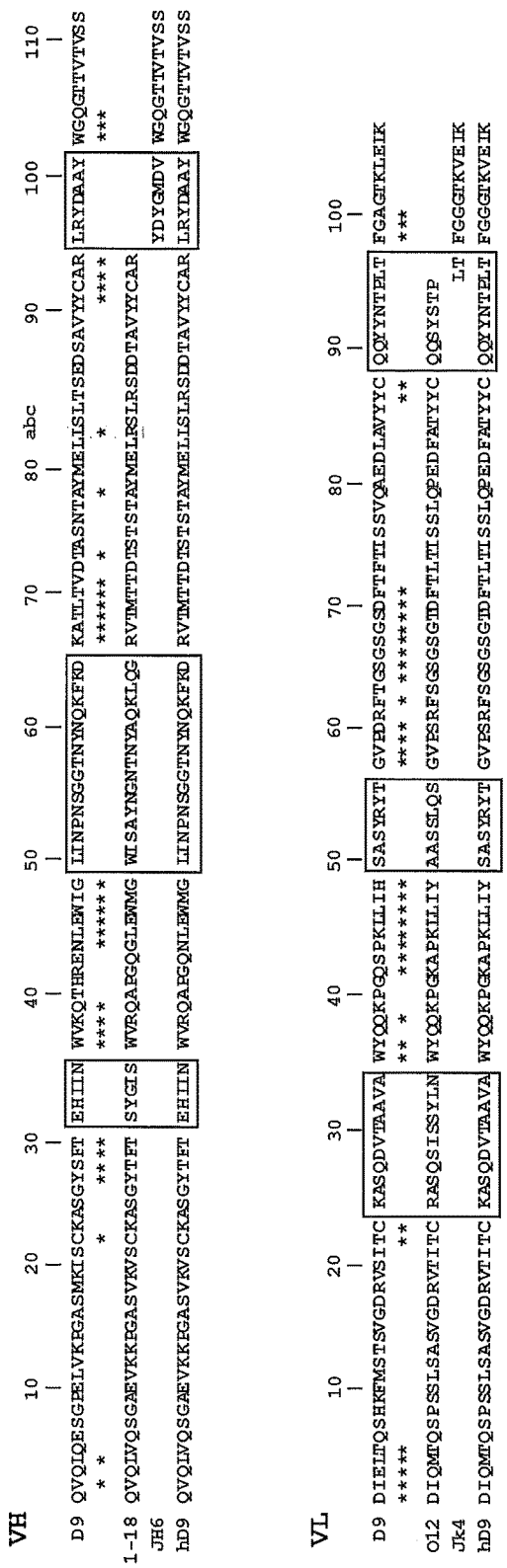
FIG. 5 depicts humanization of mouse D9 Fv by CDR-grafting. Residues are numbered according to Kabat. CDRs are marked with unshaded boxes. Key FR residues are marked with *. Two key FR residues in D9 VH, which are kept in hD9 VH are marked with shaded boxes. VH D9 (SEQ ID N0:32); VH 1-18 (SEQ ID N0:37); VH JH6 (SEQ ID N0:38); VH hD9 (SEQ ID NO:41); VL D9 (aa 1-107 of SEQ ID NO:31); VL 012 (SEQ ID N0:39); VL Jk4 (SEQ ID N0:40) and VL hD9 (SEQ ID N0:42).

CDR-grafted antibodies tend to lose the parental binding affinity. The key for CDR-grafted antibodies to remain the parental binding affinity lies in the preservation of the murine CDR conformation in the humanized antibody for antigen binding. The CDR conformation is mainly dependent on CDR canonical structures determined by a few canonical conserved residues located in CDRs and FRs. Furthermore, some key resides in FRs fine-tune the CDR conformation. They include vernier zone resides, forming a layer underlying the CDRs and interchain packing resides, pairing of CDRs of VH and VL. In order to determine those key FR residues, the molecular model of D9 variable region was established through PIGS (http://www.biocomputing.it/pigs), a web server for the automatic modeling of immunoglobulin variable domains based on the most homologous antibody VH (2NR6), sharing 86% identity and VL (1MLB), sharing 70% identity with the corresponding VH and VL of D9 in the database of known immunoglobulin structure. Three D structure of D9 was then visualized using a pdb molecular visualisation programme (Deepview), the vernier zone residues located in 5 Å of the CDRs and the interchain packing resides located in 5 Å of VH-VL interface were identified shown in FIG. 5.

Humanization of D9 mAb

There are two sources of human antibody sequences: mature and germline. The latter has two advantages over the former as FR donors for murine CDR grafting. The first is less immunogenic, unlike the mature sequences that carry somatic mutations for affinity maturation generated by random processes, resulting in potential immunogenicity. The other is more flexible, resulting in more compatibility between murine CDRs and human FRs. Therefore, human germline antibody sequences have increasingly been utilized as source of FR donors.

In order to select germline human antibody VH, JH and VL, JL candidates as FR donors for D9 humanization, D9 CDR canonical structures were determined first based on identification of unique residues both in CDRs and FRs, and then formed a shortlist of germline human antibody VH and VL candidates. Those had the same or closely related canonical structures as D9 to ensure that the human antibody FR supports the mouse CDR canonical structures. Next, within the shortlist of germline human antibody VH and VL, those with highest homology CDRs and key residues in FR 1-3 were chosen as FR 1-3 donors. Human JH and JL were chosen based on highest homology to CDR3 and key residues in FR 4. Consequently, human VH gene 1-18, JH gene 6 were selected as FR donors for humanization of D9 VH; human Vk gene 012 and Jk gene 4 were selected as FR donors for humanization of D9 VL domain shown in FIG. 5. Seventy-five % of the key FR resides of D9 was the same as human donor antibodies. Another 22% were different between murine D9 and human donors, but these were conservative substitutions in the same groups of amino acids, such as S=>T (polar, non-aromatic with hydroxyl R-groups), K=>R or E=>Q or Q=>K (polar, hydrophilic), I=>M or A=>V or L=>M (non-polar, hydrophobic), H=>Y (polar, aromatic), V=>T (β-C containing branch), S=>A (tiny), D=>S (polar). The remaining 3% (2 residues) were not conserved, these being VH44 (mouse N versus human G) and VH82a (mouse L versus human R). Most importantly, VH44-N was an unusual interchain packing residue. Only 0.3% VH have N in position 44, indicating it came from somatic mutation, which might enhance antibody binding. VH82a-L was a vernier zone residue. Advantageously, molecular modeling revealed both of these as not solvent accessible, indicating these are not located on the surface of Fv and might not elicit an immune response in human. Therefore, when the CDRs of D9 were grafted onto the donor human antibody FRs, VH44-N and VH82a-L were kept in the humanized D9 (hD9).

Expression and Purification of hD9

Figure 6:
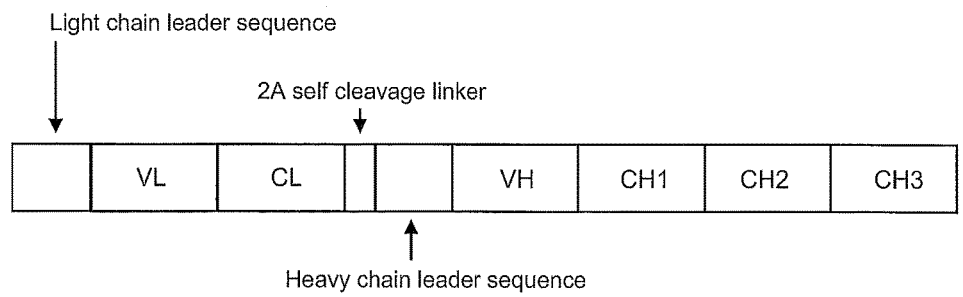
FIG. 6 depicts a schematic diagram of the hD9 gene layout.

The VH of hD9 was further grafted onto the human gamma 1 heavy chain CHs to form a complete heavy chain, while the VL was grafted onto the human kappa 1 light chain CL to form a whole humanized light chain (FIG. 6). Furthermore, a foot-and-mouth-disease virus-derived 2A self-processing sequence was introduced between heavy and light chain DNA sequences to express a full-length antibody from a single open reading frame driven by a single promoter in an adenoviral vector. To get the expressed hD9 to be secreted to culture media, a leader sequence was added upstream to the VH and VL respectively. The whole DNA sequence including the human antibody kappa light chain 012 leader sequence, the humanized light chain (VL+CL), 2A linker, 1-18 heavy chain leader sequence, and humanized heavy chain (VH+CH1+CH2+CH3), around 2 kb was synthesized as shown in FIG. 6 and then cloned into an adenoviral vector for expression.

Figure 7:
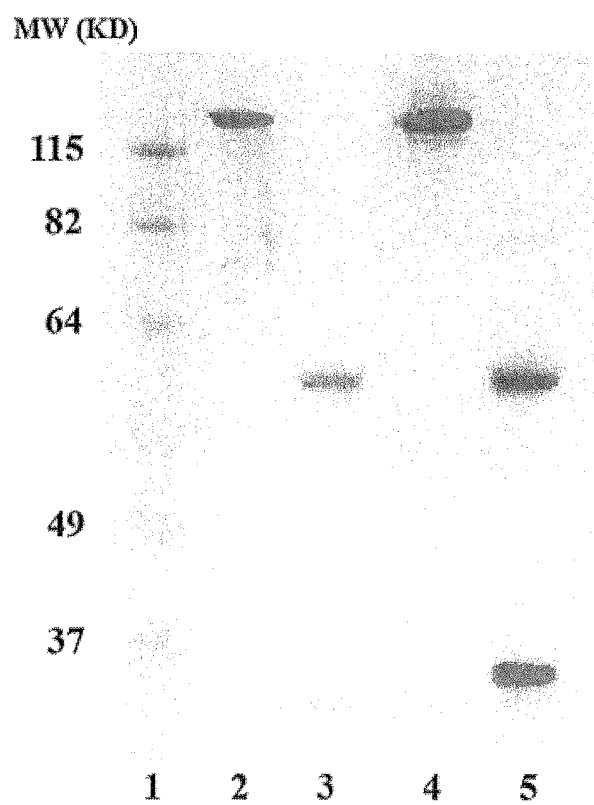
FIG. 7 SDS-PAGE analysis of purified hD9. Samples were resolved by SDS-PAGE. Lane 1 is a molecular marker; lanes 2 and 4 are control human IgG1 and hD9 in non-reducing conditions; lanes 3 and 5 are control human IgG1 and hD9 in reducing conditions.

After the recombinant hD9 was expressed in mammalian cells and purified using an ImmunoPure Protein (L) agarose column, the purified product was subjected to 10% SDS-PAGE. One obvious band of about 150 kDa in non-reducing conditions and two clear bands of about 50 kDa (heavy chain) and about 25 kDa (light chain) in reducing conditions (cleavage of disulfide bridges) were observed (FIG. 7), indicating the heavy and light chain of the recombinant hD9 was cleaved completely and properly dimerized.

Affinity Characterization of hD9

To evaluate the binding affinity of hD9, a surface plasmon resonance (SPR) biosensor was used. Ricin was captured on a biosensor chip, various concentrations of hD9 or D9 were passed through the flow cell, and the binding kinetics was recorded. The kinetic rate constants $k_{on}$ and $k_{off}$ were calculated from the ascending rate of resonance units during association and the descending rate during dissociation. The KD of hD9 or D9 for ricin was determined from the ratio of $k_{off}/k_{on}$. As shown in Table 6, hD9 had high affinity to ricin with KDs of 1.63 nM, even higher than D9 (2.56 nM), indicating humanization of D9 is successful.

TABLE 6

Comparison of kinetic constants binding to ricin between of D9 and hD9.

| Antibody | $K_{on}$ (M$^{-1}$S$^{-1}$) | $K_{off}$ (S$^{-1}$) | KD (nM) |
|---|---|---|---|
| hD9 | 4.19 × 10$^5$ | 6.8 × 10$^{-4}$ | 1.63 |
| D9 | 1.835 × 10$^5$ | 4.7 × 10$^{-4}$ | 2.56 |

Efficacy Evaluation of hD9

To evaluate hD9 efficacy in vivo, ricin was given at the dose of 5×LD50 to mice by i.p route. hD9 at the dose of 5 μg was administered by the i.p. route at 2, 4, 6 hr after ricin challenge. hD9 could rescue mice up to 6 hr post-challenge, allowing 50% mouse survival (Table 7), comparable to D9, which showed 100% protection up to 6 hr post-challenge. This humanized D9 has potential use for prophylactic or therapeutic purposes against ricin poisoning.

TABLE 7

Survival of mice administered hD9 at varying time points after received 5 × LD50 of ricin. The number of viable mice on each day following administration of antibody is given.

| | Time points | Day 1 | Day 2 | Day 3 | Day 4 | Day 5 | Day 6 | Day 7 |
|---|---|---|---|---|---|---|---|---|
| hD9 5 μg per mouse | 2 hr | 8 | 8 | 8 | 8 | 8 | 8 | 8 |
| | 4 hr | 8 | 8 | 8 | 8 | 8 | 8 | 8 |
| | 6 hr | 8 | 8 | 8 | 8 | 8 | 4 | 4 |

REFERENCES

All patents, patent applications and publications referred to herein and throughout the application are hereby incorporated by reference in their entirety.

Audi J, Belson M, Patel M, Schier J, Osterloh J. Ricin poisoning: a comprehensive review. JAMA. 2005 Nov. 9; 294(18):2342-51.

Burnett J C, Henchal E A, Schmaljohn A L, Bavari S. The evolving field of biodefence: therapeutic developments and diagnostics. Nat Rev Drug Discov. 2005 April; 4(4): 281-97.

Chothia C, Lesk A M. Canonical structures for the hypervariable regions of immunoglobulins. J Mol Biol. 1987; 196(4):901-17.

de Kruif, J. & Logtenberg, T. Leucine zipper dimerized bivalent and bispecific scFv antibodies from a semi-synthetic antibody phage display library. J Biol Chem 271, 7630-7634 (1996).

Eisenberg, D.; E. Schwarz; M. Komaromy & R. Wall (1984) Analysis of membrane and surface protein sequences with the hydrophobic moment plot. J Mol Biol, 179, 125-142

Fang J, Qian J J, Yi S, Harding T C, Tu G H, VanRoey M, Jooss K. Stable antibody expression at therapeutic levels using the 2A peptide. Nat Biotechnol. 2005 May; 23(5): 584-90.

Foxwell B M, Detre S I, Donovan T A, Thorpe P E. The use of anti-ricin antibodies to protect mice intoxicated with ricin. Toxicology. 1985 January; 34(1):79-88.

Furukawa-Stoffer, T. L., Mah, D. C. W., Cherwonogrodzky, J. W., Weselake, R. J. 1999. A novel biological-based assay for the screening of neutralizing antibodies to ricin. Hybridoma 18:505-511.

Guo J, Shen B, Sun Y, Yu M, Hu M. A novel neutralizing monoclonal antibody against both ricin toxin A and ricin toxin B, and application of a rapid sandwich enzyme-linked immunosorbent assay. Hybridoma. 2006 August; 25(4):225-9

Hewetson J F, Rivera V R, Creasia D A, Lemley P V, Rippy M K, Poli M A. Protection of mice from inhaled ricin by vaccination with ricin or by passive treatment with heterologous antibody. Vaccine. 1993; 11(7):743-6.

Kabat E A, Wu T T. Identical V region amino acid sequences and segments of sequences in antibodies of different specificities. Relative contributions of VH and VL genes, minigenes, and complementarity-determining regions to binding of antibody-combining sites. J Immunol. 1991; 147:1709-19.

Lin J Y, Liu S Y. Studies on the antitumor lectins isolated from the seeds of *Ricinus communis* (castor bean). Toxicon. 1986; 24(8):757-65.

Merritt, E. A. & Hol, W. G. AB5 toxins. *Current opinion in structural biology* 5, 165-171 (1995).

Miller D J, Ravikumar K, Shen H, Suh J K, Kerwin S M, Robertus J D. Structure-based design and characterization of novel platforms for ricin and shiga toxin inhibition. J Med Chem. 2002 Jan. 3; 45(1):90-8.

Montanaro L, Sperti S, Stirpe F. Inhibition by ricin of protein synthesis in vitro. Ribosomes as the target of the toxin. Biochem J. 1973 November; 136(3):677-83.

Neal L M, O'Hara J, Brey R N 3rd, Mantis N J. A monoclonal immunoglobulin G antibody directed against an immunodominant linear epitope on the ricin A chain confers systemic and mucosal immunity to ricin. Infect Immun. 2010 January; 78(1):552-61. Epub 2009 Oct. 26.

Nielsen, U. B., Adams, G. P., Weiner, L. M. & Marks, J. D. Targeting of bivalent anti-ErbB2 diabody antibody fragments to tumor cells is independent of the intrinsic antibody affinity. Cancer Research 60, 6434-6440 (2000).

Padlan, E. A. Anatomy of the antibody molecule. Molecular immunology 31, 169-217 (1994).

Ridgway, J. B., Presta, L. G. & Carter, P. 'Knobs-into-holes' engineering of antibody CH3 domains for heavy chain heterodimerization. Protein Eng 9, 617-621 (1996).

Smallshaw J E, Richardson J A, Vitetta E S. RiVax, a recombinant ricin subunit vaccine, protects mice against ricin delivered by gavage or aerosol. Vaccine. 2007 Oct. 16; 25(42):7459-69. Epub 2007 Aug. 30.

Sun L K, Curtis P, Rakowicz-Szulczynska E, Ghrayeb J, Chang N, Morrison S L, Koprowski H. Chimeric antibody with human constant regions and mouse variable regions directed against carcinoma-associated antigen 17-1A. Proc Natl Acad Sci USA. 1987 January; 84(1):214-8.

Zhang, J. et al. Pentamerization of single-domain antibodies from phage libraries: a novel strategy for the rapid generation of high-avidity antibody reagents. *J Mol Biol* 335, 49-56 (2004).

International PCT Publication No. WO2003/046560, U.S. Pat. Nos. 6,180,370, 5,693,761, 6,054,297, 5,859,205, 5,869,619, 5,766,886, 5,821,123, European Patent No. 519596 and European Patent No. 626390.

The invention claimed is:

1. A method of preventing deleterious effects caused by ricin exposure or of treating exposure to ricin, comprising administering
   an antibody or fragment thereof, or
   a composition comprising an antibody or fragment thereof and a pharmaceutically acceptable diluent, excipient, or carrier
to a subject in need thereof, wherein the antibody or fragment thereof comprises a CDR L1 of sequence KASQDVTAAVA (SEQ ID NO:4), a CDR L2 of sequence SASYRYT (SEQ ID NO:8), and a CDR L3 of sequence QQYYNTPLT (SEQ ID NO:12); and a variable heavy chain comprising CDR H1 of sequence EHIIN (SEQ ID NO:16), a CDR H2 of sequence LINPNSGGTNYNQKFKD (SEQ ID NO:20), and a CDR H3 of sequence LRYDAAY (SEQ ID NO:24), and wherein the antibody or fragment thereof specifically binds ricin toxin lectin-B protein.

2. The method of claim 1, wherein the subject is a mouse or a human.

3. The method of claim 1, wherein the antibody or fragment thereof comprises
   the variable light chain sequence:

(SEQ ID NO: 31)
DIELTQSHKFMSTSVGDRVSITCKASQDVTAAVAWYQQKPGQSPKLLIHS

ASYRYTGVPDRFTGSGSGSDFTFTISSVQAEDLAVYYCQQYYNTPLTFGA

GTKLELKR or a sequence at least 95% identical thereto;
and the variable heavy chain sequence:

(SEQ ID NO: 32)
QVQLQESGPELVKPGASMKISCKASGYSFTEHIINWVKQTHRENLEWIGL

INPNSGGTNYNQKFKDKATLTVDTASNTAYMELLSLTSEDSAVYYCARLR

YDAAYWGQGTTVTVSS, or a sequence at least 95% identical thereto.

4. The method of claim 1, wherein the antibody or fragment thereof of claim 1, is an IgG.

5. The method of claim 1, wherein the one or more than one antibody or fragment thereof is administered to the subject several hours following exposure to the ricin toxin to treat ricin exposure.

6. The method of claim 1, wherein the one or more than one antibody or fragment thereof is administered to the subject several weeks prior to exposure to the ricin toxin to protect the subject against ricin exposure.

7. The method of claim 1, further comprising administering a second antibody or fragment thereof said second antibody or fragment thereof comprising the variable light chain sequence:

(SEQ ID NO: 27)
DIVLTQSPSSMYASLGERVTITCKASQDINNYLRWFQQKPGKSPKTLIYR

ANRLVDGVPSRFSGSGSGQDYSLTISSLEYEDMGFYSCLQYDEFPYTFGG

GTKLEIKR or a sequence at least 95% identical thereto;
and the variable heavy chain sequence:

(SEQ ID NO: 23)
QVQLQESGPELVKPGASMKISCKASGYSFTEHIINWVKQTHRENLEWIGL

INPNSGGTNYNQKFKDKATLTVDTASNTAYMELLSLTSEDSAVYYCARLR

YDAAYWGQGTTVTVSS, or a sequence at least 95% identical thereto.

8. The method of claim 7, wherein at least one of the antibodies or fragments thereof is humanized.

9. The method of any one of claim 1-4, wherein preventing deleterious effects caused by ricin exposure is achieved by conferring immunity against ricin by administering the antibody or fragment thereof prior to exposure.

10. The method of claim 9, wherein administering the antibody or fragment thereof occurs at least 1 day prior to exposure.

* * * * *

UNITED STATES PATENT AND TRADEMARK OFFICE
CERTIFICATE OF CORRECTION

PATENT NO. : 10,081,672 B2  
APPLICATION NO. : 15/088944  
DATED : September 25, 2018  
INVENTOR(S) : Hu et al.

Page 1 of 1

It is certified that error appears in the above-identified patent and that said Letters Patent is hereby corrected as shown below:

In the Specification

Column 19, Line 37-40, replace:
"EVQLQESGTGLVKPGASVKLSCKASGYTFT<u>EYIIN</u>VVVKQRSGQGLEWIG<u>WFYPGSGDIKYNEKFKD</u>KATLTADKSSSTVYMELSRLTSEDSAVYFCAR<u>NGRWDDDYFDY</u>WGQGTTVTVSS"
With:
--EVQLQESGTGLVKPGASVKLSCKASGYTFT<u>EYIIN</u>WVKQRSGQGLEWIG<u>WFYPGSGDIKYNEKFKD</u>KATLTADKSSSTVYMELSRLTSEDSAVYFCAR<u>NGRWDDDYFDY</u>WGQGTTVTVSS--

In the Claims

Column 50, Lines 33-38, Claim 7, replace:
"(SEQ ID NO: 23) QVQLQESGPELVKPGASMKISCKASGYSFTEHIINWVKQTHRENLEWIGLINPNSGGTNYNQKFKDKATLTVDTASNTAYMELLSLTSEDSAVYYCARLRYDAAYWGQGTTVTVSS,"
With:
--(SEQ ID NO: 28) EVQLQESGTGLVKPGASVKLSCKASGYTFTEYIINWVKQRSGQGLEWIGWFYPGSGDIKYNEKFKDKATLTADKSSSTVYMELSRLTSEDSAVYFCARNGRWDDDYFDYWGQGTTVTVSS,--

Signed and Sealed this  
Twentieth Day of August, 2019

Andrei Iancu  
*Director of the United States Patent and Trademark Office*